United States Patent [19]

Ellman

[11] Patent Number: 5,288,514
[45] Date of Patent: Feb. 22, 1994

[54] SOLID PHASE AND COMBINATORIAL SYNTHESIS OF BENZODIAZEPINE COMPOUNDS ON A SOLID SUPPORT

[75] Inventor: Jonathan A. Ellman, Berkeley, Calif.

[73] Assignee: The Regents of the University of California, Oakland, Calif.

[21] Appl. No.: 944,469

[22] Filed: Sep. 14, 1992

[51] Int. Cl.$^5$ ............................................. A01N 1/02
[52] U.S. Cl. ........................................ 427/2; 530/334; 530/337; 530/345
[58] Field of Search ..................... 427/2; 530/334, 335, 530/337, 345

[56] References Cited

U.S. PATENT DOCUMENTS

| | | | |
|---|---|---|---|
| 4,968,794 | 11/1990 | Weber et al. | 540/560 |
| 5,082,839 | 1/1992 | Weber et al. | 514/220 |
| 5,143,854 | 9/1992 | Pirrung et al. | 436/518 |

FOREIGN PATENT DOCUMENTS

WO92/10092 6/1992 PCT Int'l Appl. ............ A01N 1/02

OTHER PUBLICATIONS

Jung et al., "Multiple Peptide Synthesis Methods and Their Applications," *Angew. Chem. Int. Ed. Engl.* 31, 367–383, 1992.

Evans et al., "Design of Nonpeptidal Ligands for a Peptide Receptor: Cholecystokinin Antagonists," *J. Med. Chem.* 30, 1229–1239, (1987).

Sternbach, "The Benzodiazepine Story," *J. Med. Chem.* 22, 1–7, (1979).

Fodor et al., "Light-Directed, Spatially Addressable Parallel Chemical Synthesis," *Science* (1991) 251:767–773.

Lam et al., "A new type of synthetic peptide library for identifying ligand-binding activity," *Nature* (1991) 354:82–84.

Houghten et al., "Generation and use of synthetic peptide combinatorial libraries for basic research and drug discovery," *Nature* (1991) 354:84–86.

Wetzel, "Commentary: Learning from the immune system: laboratory methods for creating and refining molecular diversity in polypeptides," *Protein Engineering* (1991) 4:371–374.

Evans et al., "Design of potent, orally effective, non-peptidal antagonists of the peptide hormone cholecystokinin," *Proc. Natl. Acad. Sci.* (1986) 83:4918–4922.

Romer et al., "An opioid benzodiazepine," *Nature* (1982) 298:759–760.

Pauwels et al., "Potent and selective inhibition of HIV-1 replication *in vitro* by a novel series of TIBO derivatives," *Nature* (1990) 343:470–474.

Hsu et al., "Inhibition of HIV Replication in Acute and Chronic Infections in Vitro by a Tat Antagonist," *Science* (1991) 254:1799–1802.

Atherton et al., "Peptide synthesis. Part 2. Procedures of Solid-phase Synthesis using Nα-Fluorenylmethoxycarbonylaminoacids on Polyamide Supports. Synthesis of Substance P and of Acyl Carrier Protein 65–74 Decapeptide,"*J. Chem. Soc.* Perkin I (1981) 538–546.

Carpino et al., "((9-Fluorenylmethyl)oxy)carbonyl (FMOC) Amino Acid Fluorides. Convenient New Peptide Coupling Reagents Applicable to the FMOC/*ter*-*t*-Butyl Strategy for Solution and Solid-Phase Syntheses," *J. Am. Chem. Soc.* (1990) 112:9651–9652.

(List continued on next page.)

*Primary Examiner*—Asok Pal
*Assistant Examiner*—P. Achutamurthy
*Attorney, Agent, or Firm*—Townsend and Townsend Khourie and Crew

[57] ABSTRACT

Methods, compositions, and devices for synthesis of therapeutically useful compounds. The invention provides a rapid approach for combinatorial synthesis and screening of libraries of derivatives of therapeutically important classes of compounds such as benzodiazepines, prostaglandins and β-turn mimetics. In order to expediently synthesize a combinatorial library of derivatives based upon these core structures, general methodology for the solid phase synthesis of these derivatives is also provided. This disclosure thus also describes an important extension of solid phase synthesis methods to nonpolymeric organic compounds.

18 Claims, 4 Drawing Sheets

OTHER PUBLICATIONS

Pirkle et al., "Direct Liquid Chromatographic Separation of Benzodiazepinone Enantiomers," *J. Chromat.* (1984) 291:291-298.

Geysen et al., "Strategies for epitope analysis using peptide synthesis," *J. Immunol. Meth.* (1987) 102:259-274.

Hokfelt et al., "Distribution Patterns of CCK and CCK mRNA in some Neuronal and Non-Neuronal Tissues," *Neuropeptides* (1991) 19(Sup):31-43.

Woodruff et al., "Functional Role of Brain CCK Receptors," *Neuropeptides* (1991) 19(Sup):45-56.

Chang et al., "Biochemical and pharmacological characterization of an extremely potent and selective nonpeptide cholecystokinin antagonist," *Proc. Natl. Acad. Sci.* (1986) 4923-4926.

Davis et al., "A convergent Total Synthesis of ($\pm$)-Prostaglandin $F_{2\alpha}$ via Conjugate Addition and Regiospecific Enolate Trapping," *J. Org. Chem.* (1979) 44:3755-3759.

Suzuki et al., "The Three-Component Coupling Synthesis of Prostaglandins," *J. Am. Chem. Soc.* (1988) 110:4718-4726.

Taylor, "Organocopper Conjugate Addition-Enolate Trapping Reactions," *Synthesis* (1985) 364-392.

Lu et al., "Improved Synthesis of 4-Alkoxybenzyl Alcohol Resin," *J. Org. Chem.* (1981) 46:3433-3436.

Rose et al., "Turns in Peptides and Proteins," *Advances in Protein Chem.* (1985) 37:1-109.

Ball et al., "Conformational Constraints: Nonpeptide $\beta$-Turn Mimics," *J. of Molecular Recognition* (1990) 3:55-64.

Evans et al., "The Total Syntheses of the Isodityrosine-Derived Cyclic Tripeptides OF4949-III and K-13. Determination of the Absolute Configuration of K-13," *J. Am. Chem. Soc.* (1989) 111:1063-1072.

Saragovi et al., "Design and Synthesis of a Mimetic from an Antibody Complementarity-Determining Region," *Science* (1991) 253:792-795.

Spatola et al., "Synthesis and Biological Activities of Pseudopeptide Analogues of LH-RH: Agonists and Antagonists," *Biochem. and Biophys. Res. Comm.* (1980) 97:1014-1023.

Yankeelov, Jr. et al., "Peptide-Gap Inhibitors. 2. Stereo-selective Synthesis of Enantiomeric Dipeptide Analogues of Glycylleucine Which Contain Methylene Thioether Groups Substituted for Peptide Linkages," *J. Org. Chem.* (1978) 43:1623-1624.

Spatola et al., "Pseudodipeptides: A Novel Route to Serine-Containing Diasteromeric Analogues," *J. Org. Chem.* (1981) 46:2393-2394.

Felix et al., "Applications of BOP reagent in solid phase synthesis," *Int. J. Peptide Protein Res.* (1988) 31:231-238.

Felix et al., "Synthesis, biological activity and conformational analysis of cyclic GRF analogs," *Int. J. Peptide Protein Res.* (1988) 32:441-454.

Evans et al. (1988) J. Med. Chem. 31:2235-2246.

Bunin et al. (1992) J. Am. Chem. Soc. 114:10997-10998.

Camps et al. (1975) Chem. Abstr. 83:841, Abst. #10018q.

Camps et al. (1977) Chem. Abstr. 87:30, Abst. #118496r.

Camps et al. (1977) Chem. Abstr. 87:542, Abst. #151641g.

Camps et al. (1971) Chem. Abstr. 75:18, Abst. #36925t.

Camps et al. (1971) Chem. Abstr. 75:19, Abst. #36938z.

Camps et al. (1974) Chem. Abstr. 81:418, Abst. #63015b.

Camps et al. (1971) Tett. Lett. 20:1713-1714.

Camps et al. (1971) Tett. Lett. 20:1715-1716.

Baum (1993) "Solid-phase synthesis of benzodiazepines" Chemical and Engineering News, Jan. 18, pp. 33-34.

SOLID PHASE AND COMBINATORIAL SYNTHESIS OF BENZODIAZEPINE COMPOUNDS ON A SOLID SUPPORT

BACKGROUND OF THE INVENTION

The present invention relates to the field of solid phase chemistry. More specifically, in one embodiment the invention provides a method, device, and compositions for solid phase and combinatorial synthesis of organic compounds and, most particularly, therapeutically important classes of compounds such as benzodiazepines, prostaglandins, and B-turn mimetics.

Obtaining a better understanding of the important factors in molecular recognition in conjunction with developing potent new therapeutic agents is a major focus of scientific research. Chemical and biological methods have recently been developed for the generation of large combinatorial libraries of peptides and oligonucleotides that are then screened against a specific receptor or enzyme in order to determine the key molecular recognition elements of the biopolymer for that receptor or enzyme. Unfortunately, peptides and oligonucleotides tend to have limited oral activities and rapid clearing times. Therefore, such materials tend to have limited utility as bioavailable therapeutic agents.

Virtually any bioavailable organic compound can be accessed by chemical synthesis; however, such organic compounds are still synthesized and evaluated one at a time in many cases, thus dramatically limiting the number of derivatives which can be studied.

This limitation could be overcome by developing the methodology for the combinatorial synthesis of large numbers of derivatives of therapeutically important classes of bioavailable organic compounds. Screening these compounds against key receptors or enzymes would then greatly accelerate the acquisition of useful structure versus recognition data and would revolutionize the search for potent new therapeutic agents.

From the above it is seen that improved methods, compositions, and devices for synthesis of therapeutically useful compounds are desired.

SUMMARY OF THE INVENTION

Improved methods, compositions, and devices for synthesis of therapeutically useful compounds are provided by virtue of the present invention. The invention provides a rapid approach for combinatorial synthesis and screening of libraries of derivatives of three therapeutically important classes of compounds in specific embodiments; benzodiazepines, prostaglandins and β-turn mimetics. In order to expediently synthesize a combinatorial library of derivatives based upon these core structures, general methodology for the solid phase synthesis of these derivatives is also provided. When synthesis on solid support proceeds according to preferred aspects of the present invention, purification and isolation steps can be eliminated thus dramatically increasing synthesis efficiency. This patent disclosure thus also describes an important extension of solid phase synthesis methods to nonpolymeric organic compounds.

A further understanding of the nature and advantages of the inventions herein may be realized by reference to the remaining portions of the specification and the attached drawings.

DESCRIPTION OF THE PREFERRED EMBODIMENTS

CONTENTS

Figure 1:
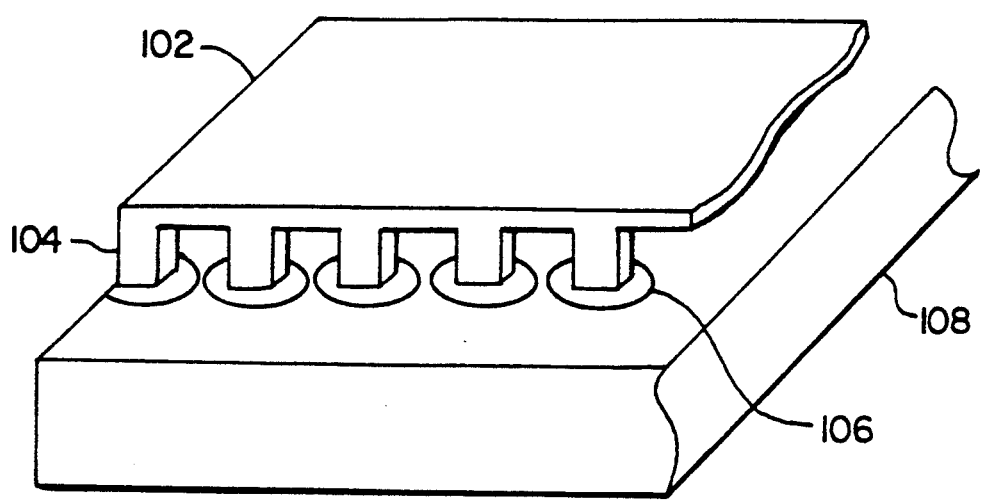
FIG. 1 is an illustration of pin based synthesis techniques.

I. General
  A. Terminology
  B. Overall Description of the Invention
II. Benzodiazepines
  A. Description
  B. Examples
III. Prostaglandins
  A. Description
  B. Examples
IV. β-Turn Mimetics
  A. Description
  B. Examples
V. Pin Based Synthesis
VI. Bead Based Synthesis
VII. Light Directed Synthesis
VIII. Conclusion

I. General

A. Terminology

The following terms are intended to have the following general meanings:

1. Complementary: Refers to the topological compatibility or matching together of interacting surfaces of a ligand molecule and its receptor. Thus, the receptor and its ligand can be described as complementary, and furthermore, the contact surface characteristics are complementary to each other.

2. Ligand: A ligand is a molecule that is recognized by a particular receptor. Examples of ligands that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, cofactors, drugs, lectins, sugars, oligonucleotides (such as in hybridization studies), nucleic acids, oligosaccharides, proteins, and monoclonal antibodies.

3. Benzodiazepines: A seven-membered organic ring with two nitrogens in the ring, normally with nitrogens at positions 1 and 4, often with an aromatic ring attached to the seven-membered ring, normally at positions 6 and 7. Benzodiazepines include compounds having a 5-phenyl-3H-1,4-benzodiazepin-2(1H)-one nucleus, including those with substitutions at the 1-, 3-, 5- and 6- through 9-positions. Many of these compounds will have a phenyl ring at the 5-position, thereby resulting in two phenyl rings in the structure, both optionally substituted.

4. Prostaglandins: A cyclo-pentane core structure with appropriate functional groups, normally including hydroxy groups, oxo groups and/or alkyl groups extending from the ring, that produces a biological response. Prostaglandins include compounds having a 3-hydroxy-5-oxocyclopentane nucleus with variable alkyl chains, including substituted alkyls, at the 2- and 3-positions.

5. β-Turn: β-turns are normally described as a reverse in the direction of a peptide chain which takes place over about four amino acid residues. β-turn mimetics are small to medium size cyclic ring structures that mimic the structure of the β-turn. β-turn mimetics include compounds having structures which mimic β-turns in protein structures. The compounds are generally short chains of α-amino acids with variations in the side chains and substitutions in the peptide bonds.

6. Radiation: Energy which may be selectively applied including energy having a wavelength of between $10^{-14}$ and $10^4$ meters including, for example, electron beam radiation, gamma radiation, x-ray radiation, light such as ultra-violet light, visible light, and infrared light, microwave radiation, and radio waves. "Irradiation" refers to the application of radiation to a surface.

7. Receptor: A molecule that has an affinity for a given ligand. Receptors may be naturally-occurring or synthetic molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells, or other materials), drugs, oligonucleotides, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to microorganism receptors, enzymes, catalytic polypeptides, hormone receptors, and opiate receptors.

8. Substrate: A material having a rigid or semi-rigid surface, generally insoluble in a solvent of interest such as water. In some embodiments, at least one surface of the substrate will be substantially flat, although in some embodiments it may be desirable to physically separate synthesis regions for different polymers with, for example, wells, raised regions, etched trenches, or the like. According to other embodiments, small beads may be provided on the surface which may be released upon completion of the synthesis, or individual beads may be used ab initio.

9. Protecting group: A material which is chemically bound to a monomer unit and which may be removed upon selective exposure to an activator such as a selected chemical activator such as an acidic or basic environment, or to another selected activator such as electromagnetic radiation and, especially light, such as ultraviolet and visible light. Examples of protecting groups with utility herein include those comprising fluorenylmethyloxycarbonyl, nitropiperonyl, pyrenylmethoxycarbonyl, nitroveratryl, nitrobenzyl, and other orthonitrobenzyl groups, dimethyl dimethoxybenzyl, 5-bromo-7-nitroindolinyl, o-hydroxy-α-methyl cinnamoyl, and 2-oxymethylene anthraquinone.

10. Predefined Region: A predefined region is a localized area on a surface which is, was, or is intended to be activated for formation of a polymer. The predefined region may have any convenient shape, e.g., circular, rectangular, elliptical, wedge-shaped, etc. For the sake of brevity herein, "predefined regions" are sometimes referred to simply as "regions." A predefined region may be illuminated in a single step, along with other regions of a substrate.

11. Substantially Pure: A molecule such as a benzodiazepine is considered to be "substantially pure" within a predefined region of a substrate when it exhibits characteristics that distinguish it from molecules in other predefined regions. Typically, purity will be measured in terms of biological activity or function as a result of uniform composition. Such characteristics will typically be measured by way of binding with a selected ligand or receptor. Preferably the region is sufficiently pure such that the predominant species in the predefined region is the desired molecule. According to preferred aspects of the invention, the molecules synthesized on the pin or other structure are 5% pure, more preferably more than 10% pure, preferably more than 20% pure, more preferably more than 80% pure, more preferably more than 90% pure, more preferably more than 95% pure, where purity for this purpose refers to the ratio of the number of desired ligand molecules formed in a predefined region to the total number of molecules formed in the predefined region.

12. Activator: A material or energy source adapted to render a group active and which is directed from a source to a predefined location on a substrate, such as radiation. A primary illustration of an activator is light such as visible, ultraviolet or infrared light. Other examples of activators include ion beams, electric fields, magnetic fields, electron beams, x-ray, and the like.

13. Combinatorial Synthesis Strategy: An ordered strategy for parallel synthesis of diverse polymer sequences by sequential addition of reagents and which may normally be represented by a reactant matrix, and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which used light or other deprotecting or activating agents to remove protecting groups from materials for addition of other materials such as amino acids. In some embodiments, selected columns of the switch matrix are arranged in order of increasing binary numbers in the columns of the switch matrix. Such strategies and the representational notation therefor are discussed in Fodor et al., *Science* (1991) 251:767-773.

14. Linker: A molecule or group of molecules attached to a substrate and spacing a synthesized polymer from the substrate, such as for exposure/binding to a receptor.

15. Abbreviations: The following frequently used abbreviations are intended to have the following meanings:
BOC: t-butoxycarbonyl.
BOP: benzotriazol-1-yloxytris-(dimethylamino)-phosphonium hexafluorophosphate.
DCM: dichloromethane; methylene chloride.
DMF: dimethyl formamide.
FMOC: fluorenylmethyloxycarbonyl.
NV: nitroveratryl.
NVOC: 6-nitroveratryloxycarbonyl.
P: protective group.
THF: tetrahydrofuran.
HMPA: 2-(4-hydroxymethyl phenoxy) acetate.

B. Overall Description of the Invention

The invention provides novel approaches for the combinatorial synthesis and screening of libraries of derivatives of therapeutically important classes of compounds including 1,4-benzodiazepines, prostaglandins, and β-turn mimetics. In order to expediently synthesize a combinatorial library of derivatives based upon these core structures, generalized methodologies for the solid phase synthesis of these derivatives are also provided. Synthesis on solid support proceeds in sufficiently high yield in preferred embodiments such that purification and isolation steps can be eliminated thus dramatically increasing synthesis efficiency.

II. Benzodiazepines

A. Description

One application of the present invention is the preparation and screening, preferably in parallel and simultaneous fashion, of large numbers of benzodiazepine derivatives. Benzodiazepines are useful drugs for the targeting of enzymes, regulatory proteins and receptors of various kinds, and a variety of benzodiazepines, as well as their binding affinities, are known. Many more benzodiazepine structures may be postulated, however, and considered as potential active drugs for the same target species, and benzodiazepines as well as other drugs which target other enzymes, regulatory proteins and receptors are often sought.

To achieve the preparation and screening of large numbers of compounds that have benzodiazepine structures, the present invention provides a solid-phase synthesis method for benzodiazepines in which variable substituent groups are attached to a common central benzodiazepine structure. In the solid-phase synthesis, a benzodiazepine precursor which contains the phenyl ring of the benzodiazepine without the closed heterocyclic ring is bonded to a solid support through a linkage on the phenyl ring. Once the precursor is bonded to the solid support, a series of reactions is performed by contacting the solid support with a series of liquid-phase reagents. These reactions include closure of the heterocyclic ring and derivatization of the compound at various locations on the rings or other reactive sites on the compound structure. Appropriate protecting group(s) are attached to the precursor prior to the reaction with the solid support and to various sites on the molecule and the reagents to ensure that the desired reaction in each case occurs at the desired location on the structure.

This solid-phase synthesis permits each reaction to be confined to the surface area of a small solid structure. The physical joining of a multitude of small solid structures into a single unit, for example, then permits the simultaneous handling of a multitude of compounds and reagents. The use of structures of this kind for certain multiple simultaneous reactions is known in the art, and its application to the present invention will become apparent from the description which follows.

An overall illustration of the solid-phase synthesis of benzodiazepines is shown in Reaction Scheme I.

REACTION SCHEME I

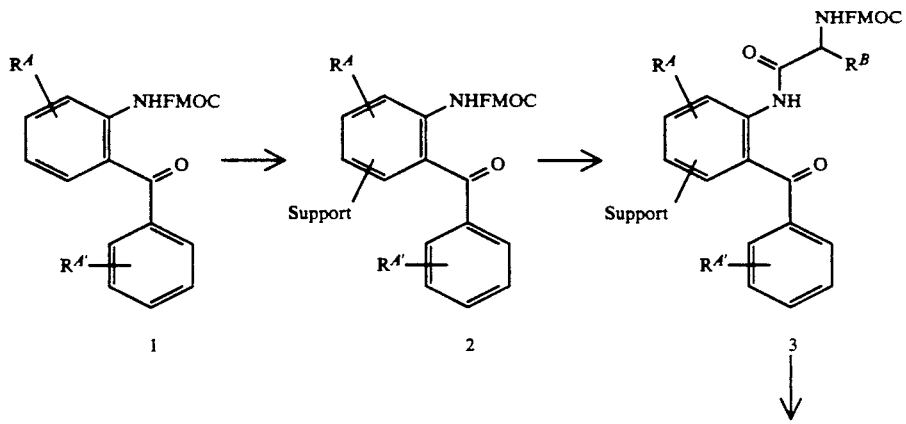

REACTION SCHEME I

-continued

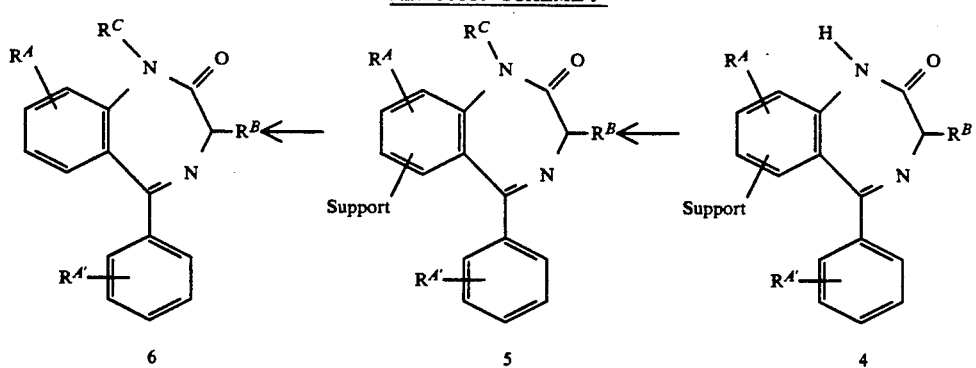

The starting material 1 is a 2-aminobenzophenone bearing substituents $R^A$ on one phenyl ring and $R^{A'}$ on the other, and in which the amino group bears the protecting group FMOC. The $R^A$ and $R^{A'}$ substituents may be varied widely in both their identity and the positions which they occupy on the phenyl rings, and can thus be studied as variables for the screening which is performed subsequent to the synthesis. Some of these substituents will be inert to reagents which are used in the succeeding steps of the synthesis for activation or derivatization of the compound at other sites on the structure, while other substituents will be susceptible to the action of such reagents or by use of appropriate protecting groups. This type of susceptibility can be avoided by the appropriate selection of less active reagents. This will be explained in more detail below.

The substituted 2-aminobenzophenone 1 is coupled to the solid support, preferably by a cleavable linker such as an acid-cleavable linker, thereby forming a support-bound substituted 2-aminobenzophenone 2. A wide variety of acid-cleavable linkers are known among those skilled in the art, as described by Atherton et al., *J. Chem. Soc. Perkin I* (1981) 538–546, incorporated herein by reference. Prominent examples are 2-(4-hydroxymethyl phenoxy) acetic acid (HMPA) and allyl 2-(4-bromomethyl phenoxy) acetate, and various analogs and derivatives of these compounds. Reaction Scheme II is an illustration of this type of coupling:

REACTION SCHEME II

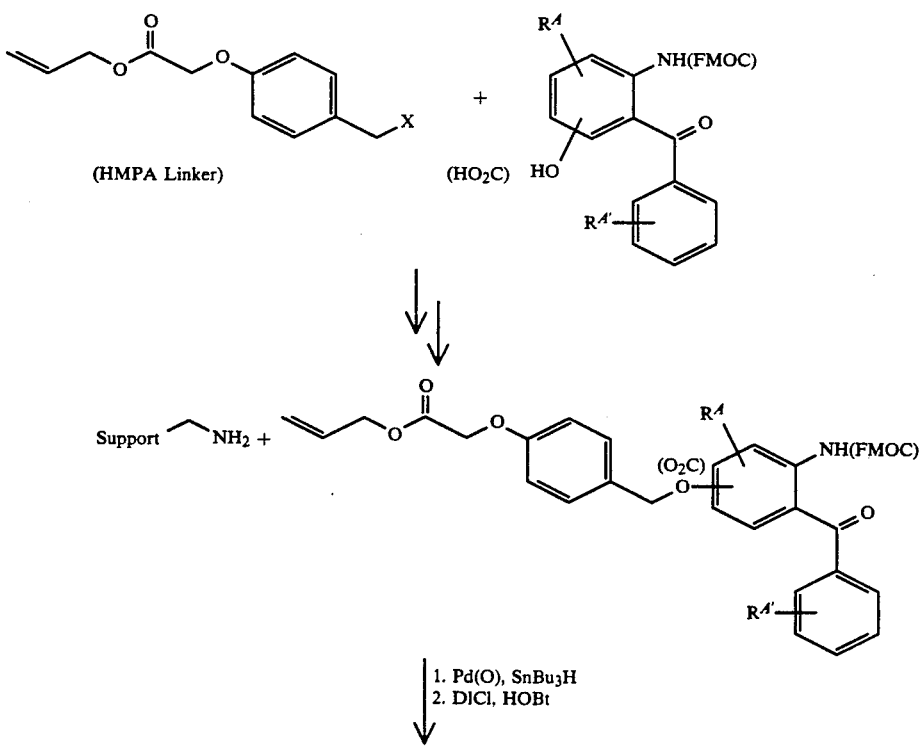

-continued
REACTION SCHEME II

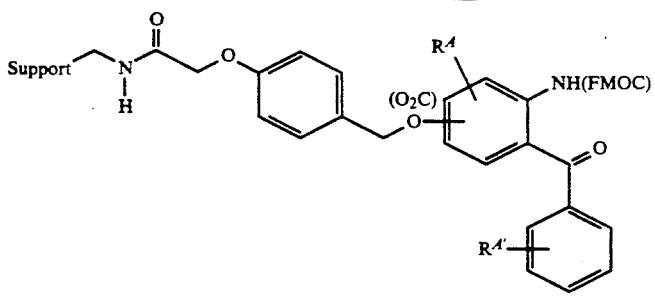

Once the coupling is achieved, the FMOC protecting group is removed by conventional means, leaving an amine group.

A wide variety of natural and unnatural amino acids with FMOC-protected amine groups are readily available from suppliers to the industry. Any one of these may be coupled to the support-bonded unprotected 2-aminobenzophenone to form an amino acid-derivatized 2-aminobenzophenone 3. This is readily accomplished by first converting the amino acid to an activated acyl fluoride derivative, which results in efficient coupling to the 2-aminobenzophenone. A discussion of this technique is found in Carpino et al., *J. Am. Chem. Soc.* (1990) 112:9651–9652. The amino acid used in Reaction Scheme I has a variable side chain $R^B$, which introduces a third site for variation of the structure of the final benzodiazepine derivative. Base-catalyzed removal of the FMOC protecting group from 3 followed by exposure to 5% acetic acid in dimethyl formamide (DMF) results in cyclization to provide the benzodiazepine structure 4.

Variation at a fourth site on the structure is achieved by alkylation of the amido nitrogen atom, i.e., at the 1-position on the benzodiazepine structure. This is accomplished by conventional techniques involving deprotonation of 4 by the use of a base followed by reaction with an alkylating agent. Examples of suitable bases are lithiated 5-phenylmethyl 2-oxazolidone in tetrahydrofuran (THF), lithium diisopropyl amide in THF, and lithium dicyclohexyl amide in THF, and in some cases depending on the susceptibility of other groups on the molecule, sodium hydride or potassium hydride in DMF. The alkylating agent may be either an activated alkylating agent such as methyl iodide or t-butyl bromoacetate, or an unactivated alkylating agent such as ethyl iodide or isopropyl iodide in the presence of DMF. The use of lithiated 5-phenylmethyl 2-oxazolidone (pKa in dimethyl sulfoxide (DMSO) 20.5) as the base for deprotonation allows alkylation of the benzodiazepine without alkylation of any groups represented by $R^A$, $R^{A'}$ or $R^B$ with higher pKa values, such as amides (pKa in DMSO of approximately 25–26), carbamates (pKa in DMSO of approximately 24.5), or esters (pKa in DMSO of approximately 30).

Still further variations in the basic benzodiazepine structure may be made. For example, the amide formed by the adjacent NH and C=O groups of the heterocyclic ring can be converted to a thioamide, the imine (i.e., the =N— on the heterocyclic ring) can be reduced to an amine, or a second alkylation can be performed on an amide or carbamate functionality present in the molecule at a location other than the amide nitrogen that has been alkylated. Each of these reactions is performed by conventional means readily apparent to those skilled in the art.

The N-alkylated benzodiazepine 5 is then optionally cleaved from the support by conventional methods for cleaving an acid-labile linkage. This may be achieved for example by treatment with 85:5:10 trifluoroacetic acid/water/dimethylsulfide.

Using this method of synthesis, a combinatorial library of benzodiazepine derivatives is constructed by methods which are analogous to any of the variety of similar methods known in the art for the synthesizing peptide derivatives.

One example of such a method is the pin method developed by Geysen et al., for combinatorial solid-phase peptide synthesis. A description of this method is offered by Geysen et al., *J. Immunol. Meth.* (1987) 102:259–274, incorporated herein by reference. According to this method as it may be practiced in the present invention, a series of 96 pins are mounted on a block in an arrangement and spacing which correspond to a 96-well Microtiter reaction plate, and the surface of each pin is derivatized to contain terminal aminomethyl groups. The pin block is then lowered over a series of reaction plates in sequence to immerse the pins in the wells of the plates where coupling occurs at the terminal aminomethyl groups and the various reactions in the reaction schemes described above are performed as discussed in greater detail below.

Reagents varying in their substituent groups occupy the wells of each plate in a predetermined array, to achieve as ultimate products a unique benzodiazepine on each pin. By using different combinations of substituents, one achieves a large number of different compounds with a common central benzodiazepine structure. For example, the synthesis may begin with ten different 2-aminobenzophenone derivatives (Compound 1 in Reaction Scheme I above, differing in terms of the substituents represented by $R^A$ and/or $R^{A'}$), and each of these ten may be reacted with different amino acids such as thirty different amino acids (differing in terms of the side chain represented by $R^B$ in Compound 3) to provide 300 different cyclic intermediates (Compound 3). Reaction of each of these 300 intermediates with fifteen different alkylating agents (as represented by the substituent $R^C$ in Compound 5) would result in 4,500 unique benzodiazepine derivatives.

Once formed in this manner, each benzodiazepine derivative may be cleaved from its pin by treatment with acid, as described above. In one preferred embodiment of the invention, each benzodiazepine derivative will be prepared in sufficient quantity for screening purposes, and for analysis by such methods as high performance liquid chromatography (HPLC) and mass spectral analysis to verify the purity and integrity of the compound. Quantities on the order of approximately 50 nanomoles will generally suffice.

The resulting benzodiazepine combinatorial library may then be screened using the pin configuration in combination with appropriately charged and indexed Microtiter plates, or with similar multiwell arrangements. A typical screening, for example, may seek to compare the derivatives in the library in terms of their ability to bind to a particular receptor. Cholecystokinin receptors, which are widely distributed throughout the central and peripheral nervous system and mediate numerous physiological responses, are one example of such a receptor. Other examples will be readily apparent to those skilled in the arts of physiology and biotechnology. The screening method is based on assays for the receptors, the chemistry of the assays being conventional and well known. Radioligand assays are one example. For cholecystokinin, for example, crude membrane homogenates are prepared with minimal effort, in accordance with the procedures described by Chang et al., *Proc. Natl. Acad. Sci.* (1986) 83:4923–4926, incorporated herein by reference, and radiolabeled cholecystokinin can be purchased from New England Nuclear, Massachusetts, U.S.A. The screening may thus be based on any type of receptor, and will identify compounds within the library which show high affinity for the particular receptor chosen.

The methods described above may be used to prepare and screen large numbers of compounds, in the hundreds, the thousands and even the ten thousands in a reasonable period of time. Synthesis may be combined with screening in various different ways to screen compounds in unusually large libraries.

As one example of a strategy for a large library, the scheme may begin by the preparation of an equimolar mixture of a variety of 2-aminobenzophenone derivatives to which a common linker is attached (such as by the first reaction of Reaction Scheme II). Each pin of the 96-well array, surface-derivatized to contain a terminal amino group, is then contacted with this equimolar mixture to effect the coupling reaction. The result is that the entire combination of 2-aminobenzophenone derivatives will be evenly distributed over the surface of each pin. Each pin will then be reacted with a unique combination of amino acyl fluoride and alkylating agent to form a first library of benzodiazepine mixtures, each mixture distinguishable by the substituents $R^B$ and $R^C$ but not by the substituents $R^A$ and $R^{A'}$ for which each mixture will contain the full range. Screening this first library will provide the optimal combination of amino acid and alkylating agent. A second library is then constructed in which each pin is derivatized with only one 2-aminobenzophenone derivative, the array of pins thus representing an array of 2-aminobenzophenone derivatives, each pin however being then reacted with the optimal amino acid and alkylating agent identified in the first library. By screening the second library, one identifies the optimal 2-aminobenzophenone derivative.

B. EXAMPLES

Two methods of coupling substituted 2-aminobenzophenones to a solid phase in accordance with Reaction Scheme II are illustrated below, in one of which the coupling is achieved through an HMPA linker by way of an ether linkage, and in the other by way of an ester linkage. This is followed by a description of a general procedure for the solid-phase synthesis of 1,4-benzodiazepines according to Reaction Scheme I, with results for each of a variety of specific structures actually prepared by the procedure. The solid-phase used in the synthesis is a particulate resin, and the description is followed by a description of how the procedures in the synthesis are translated into a pin-based protocol suitable for multiple and simultaneous reactions.

1. Formation of Linker

Allyl 2-(4-hydroxymethylphenoxy)acetate

To a flame-dried three-neck 250-mL round bottom flask fitted with stir bar and reflux condenser was added hydroxymethylphenoxyacetic acid (5.0 g, 27.5 mmol). Ethyl acetate (100 mL) was added and to the resulting solution was added diisopropylethylamine (3.55 g, 27.5 mmol) with stirring. To the resulting white slurry was added allyl bromide (3.33 g, 27.5 mmol) and the mixture was heated at reflux with stirring. After 5 hours, an additional portion of allyl bromide (2.8 g, 23 mmol) was added, and the slurry was refluxed for 12 hours. After allowing the mixture to cool to room temperature, ethyl acetate (100 mL) was added and the slurry was extracted with water (100 mL), 1N aqueous sodium bisulfate (100 mL), 1N aqueous sodium bicarbonate (100 mL), and 1N aqueous sodium chloride (100 mL), then dried over sodium sulfate and concentrated in vacuo to give pure product (5.8 g, 95% yield) which became an off-white solid upon storage at −20° C., with melting point 33.5°–34.5° C. The structure was confirmed by proton NMR, carbon-13 NMR, electron impact mass spectroscopy and elemental analysis.

Allyl 2-(4-bromomethylphenoxy)acetate

The allyl 2-(4-hydroxymethylphenoxy)acetate prepared above (3.03 g, 13.6 mmol) was dissolved in 20 mL of $CH_2Cl_2$. Triphenylphosphine (3.75 g, 14.3 mmol, 1.05 equivalents) was added and the resulting clear and colorless solution was cooled to 0° C. at which time carbon tetrabromide (4.77 g, 14,3 mmol, 1.05 equivalents) was added in one portion with stirring. The resulting yellow slurry was stirred at 0° C. for 0.5 hour. The slurry was then concentrated in vacuo followed by purification on a 5 cm×20 cm silica gel column with 60:40 $CH_2Cl_2$/hexane as the eluent. The pure product upon storing at −20° C. became a white solid, with $R_f$ 0.23 in 50:50 hexane. The structure was confirmed by proton NMR and carbon-13 NMR.

2. Attachment of Linker to Substituted 2-Aminobenzophenone Through Ether Coupling In the 2-aminobenzophenone in this example, $R^A$ is a chlorine atom at the position on the ring directly opposite the amino group. The compound does not contain a substitution corresponding to $R^{A'}$.

4-(4-(2-Amino-5-chloro-benzoyl)-phenoxymethyl) phenoxyacetic acid allyl ester A solution was formed by dissolving 2-amino-5-chloro-4′-hydroxybenzophenone (1.72 g, 8.07 mmol) in 40 mL of DMF. Potassium bis(trimethylsilyl)amide that was 0.5M in toluene (16.1 mL, 8.07 mmol, 1.0 equivalents) was added dropwise with stirring. Allyl 2-(4-bromomethylphenoxy)acetate (2.30 g, 8.07 mmol, 1.0 equivalents) was then added and the resulting orange slurry was stirred at ambient temperature for 45 minutes. The slurry was concentrated in vacuo, then diluted with $CH_2Cl_2$ (150 mL) and was extracted with 1N aqueous sodium bicarbonate (100 mL) and with 1N aqueous sodium chloride (100 mL), then dried over sodium sulfate and concentrated in vacuo to give the product as a yellow solid which was approximately 95% pure and was taken to the next step without purification. The product had $R_f$ of 0.55 in 50:50:2 ethyl acetate/hexane/triethylamine. The structure was confirmed by proton NMR, carbon-13 NMR, and electron impact mass spectroscopy.

4-(4-(5-Chloro-2-fluorenylmethoxycarbonylamino-benzoyl)phenoxymethyl)phenoxyacetic acid allyl ester The product of the preceding paragraph (4.90 g, 10.8 mmol) and pyridine (1.02 g, 13 mmol, 1.2 equivalents) were dissolved in 60 mL of $CH_2Cl_2$. The resulting yellow solution was cooled to 0° C. and fluorenylmethoxycarbonyl chloride (2.95 g, 1.14 mmol, 1.05 equivalents) was added. The resulting solution was stirred at 0° C. for 15 minutes and then at ambient temperature for 1 hour. The solution was then diluted with $CH_2Cl_2$ (150 mL) and extracted twice with 1N aqueous sodium bisulfate (100 mL) and once with 1N aqueous sodium chloride (100 mL), then dried over sodium sulfate and concentrated in vacuo to give a yellow foam. The product was purified by recrystallization from $CH_2Cl_2$ and hexanes. The structure was confirmed by proton NMR, carbon-13 NMR, FAB mass spectroscopy and elemental analysis.

4-(4-(5-Chloro-2-fluorenylmethoxycarbonylamino-benzoyl)phenoxymethyl)phenoxyacetic acid The allyl ester of the preceding paragraph (1.80 g, 2.66 mmol) was dissolved in 30 mL of $CH_2Cl_2$. Tetrakis(triphenylphosphine)palladium (65 mg, 0.056 mmol, 0.02 equivalents) was added, and after flushing the reaction flask with nitrogen gas, tributyltin hydride (0.900 g, 3.09 mmol, 1.1 equivalents) was added slowly and dropwise with stirring over 2 minutes. The reaction solution turned from bright yellow to orange over 0.5 hour. The reaction solution was then diluted with $CH_2Cl_2$ (150 mL) and was extracted three times with 0.5N aqueous hydrochloric acid (100 mL) and once with aqueous sodium chloride (100 mL), then dried over sodium sulfate and concentrated in vacuo to give an off-white solid which was recrystallized from $CH_2Cl_2$ and hexanes. The structure was confirmed by proton NMR, carbon-13 NMR, FAB mass spectroscopy and elemental analysis.

3. Coupling 2-Aminobenzophenone-Linker Complex to Solid Support

To a 30 mL peptide reaction flask was added 4-(4-(5-chloro-2-fluorenylmethoxycarbonylamino-benzoyl)-phenoxymethyl)phenoxyacetic acid (1.52 g, 2.4 mmol, 2.0 equivalents), aminomethyl resin (1.99 g, 1.19 mmol of 1% crosslinked divinylbenzene-styrene, 100 mesh size, substitution level 0.60 milliequivalents/g), and hydroxybenzotriazole monohydrate (0.808 g, 5.28 mmol, 4.4 equivalents). Anhydrous DMF (12 mL) was added to the flask and the mixture was vortexed for 0.5 hour to fully solvate the resin. Diisopropylcarbodiimide (808 mg, 5.28 mmol, 4.4 equivalents) was added by syringe. The reaction flask was stoppered and then vortexed for 24 hours at which point the ninhydrin test on approximately 10 mg of the solid support demonstrated that coupling was complete. The solvent and reagents were filtered away from the solid support and the support was rinsed five times with 20 mL DMF and five times with 20 mL $CH_2Cl_2$ (for each rinse the mixture was vortexed for at least 30 seconds before filtering off the solvent) and then dried in vacuo for 12 hours.

4. Attachment of Linker to Aminobenzophenone Through Ester Coupling

A different substituted aminobenzophenone and linker used in the preceding paragraphs are used here, with a variation in the type of connecting group joining the two together.

4-Benzoyl-6-chloro-3-fluorenylmethoxycarbonylaminobenzoic acid

A solution was prepared by diluting 3-amino-4-benzoyl-6-chlorobenzoic acid (5.59 g, 20.3 mmol) with approximately 70 mL of $CH_2Cl_2$. Chlorotrimethylsilane (5.50 g, 51 mmol, 2.5 equivalents) was added by syringe and the resulting white slurry was heated at gentle reflux for 1.5 hours. After cooling the mixture to 0° C., pyridine (3.69 g, 46.7 mmol, 2.3 equivalents) was added by syringe, immediately followed by addition of fluorenylmethoxycarbonyl chloride (5.78 g, 22.3 mmol, 1.1 equivalents). The resulting slurry was stirred for one hour under a nitrogen atmosphere. The reaction solution was then diluted with $CH_2Cl_2$ (150 mL) and was extracted three times with 1.0N aqueous sodium bisulfate (100 mL) and once with aqueous sodium chloride (100 mL), then dried over sodium sulfate and concentrated in vacuo to give a viscous oil. Pure product was obtained in 64% yield (6.50 g) as a white solid by flash chromatography with 5 cm×25 cm silica gel and 40:60 ethyl acetate and then 75:25:1 ethyl acetate/hexane/acetic acid as the eluent. The structure was confirmed by proton NMR, carbon-13 NMR, and FAB mass spectroscopy.

4-Benzoyl-6-chloro-3-fluorenylmethoxycarbonyl aminobenzoyloxymethylphenoxyacetic acid allyl ester To a flame-dried 50 mL flask fitted with stir bar was added 4-benzoyl-6-chloro-3-fluorenylmethoxycarbonylaminobenzoic acid (2.50 g, 5.02 mmol) and allyl 2-(4-bromomethylphenoxy)acetate (1.12 g, 5.02 mmol). To this was added $CH_2Cl_2$ (15 mL), followed by addition of N,N-dimethylformamide dineopentyl acetal (1.16 g, 5.02 mmol, 1.0 equivalents) by syringe. The resulting red solution was stirred for 15 hours at ambient temperature, then diluted with $CH_2Cl_2$ (150 mL), then extracted once with 1.0N sodium bisulfate (100 mL) and once with aqueous sodium chloride (100 mL), then dried over sodium sulfate and concentrated in vacuo to give a red oil. Pure product was obtained in 63% yield (2.23 g) as a pale yellow oil by flash chromatography on 5 cm×25 cm silica gel eluting with 25:75 hexane/$CH_2Cl_2$ followed by 100% $CH_2Cl_2$. The structure was confirmed by proton NMR, carbon-13 NMR, FAB mass spectroscopy and elemental analysis.

4-Benzoyl-6-chloro-3-fluorenylmethoxycarbonyl aminobenzoyloxymethylphenoxyacetic acid The product of the preceding paragraph (2.2 g, 3.13 mmol) was dissolved in 40 mL of $CH_2Cl_2$. To this was added tetrakis(triphenylphosphine)palladium (72 mg, 0.063 mmol, 0.02 equivalents), and after flushing the reaction flask with nitrogen gas, tributyltin hydride (1.00 g, 3.44 mmol, 1.1 equivalents) was added slowly dropwise with stirring over 3 minutes. The reaction solution turned from bright yellow to brown over 0.75 hour. The reaction solution was then diluted with CH$_2$Cl$_2$ (150 mL), then extracted three times with 0.5N aqueous hydrochloric acid (100 mL) and once with aqueous sodium chloride (100 mL), then dried over sodium sulfate and concentrated in vacuo to give an off-white solid which was recrystallized from CH$_2$Cl$_2$ and hexanes to provide the pure product as an off-white solid (1.60 g, 77% yield). The structure was confirmed by proton NMR, carbon-13 NMR, and FAB mass spectroscopy.

5. Coupling 2-Aminobenzophenone-Linker Complex to Solid Support

To a 30 mL peptide reaction flask was added the product of the preceding paragraph (2.0 g, 3.02 mmol, 2.0 equivalents), aminomethyl resin (1.91 g, 1.51 mmol of 1% crosslinked divinylbenzene-styrene, 200–400 mesh size, substitution level 0.79 milliequivalents/g), and hydroxybenzotriazole monohydrate (0.925 g, 6.04 mmol, 4.4 equivalents). Anhydrous DMF (10.4 mL) was added to the flask and the mixture was vortexed for 0.5 hour to fully solvate the resin. Diisopropylcarbodiimide (762 mg, 6.04 mmol, 4.4 equivalents) was added by syringe and an additional 2.0 mL of DMF was added to rinse down the sides of the peptide reaction flask. The reaction flask was stoppered and then vortexed for 24 hours at which point the ninhydrin test on approximately 10 mg of the solid support demonstrated that coupling was complete. The solvent and reagents were filtered away from the solid support and the support was rinsed five times with 20 mL DMF and five times with 20 mL CH$_2$Cl$_2$ (for each rinse the mixture was vortexed for at least 30 seconds before filtering off the solvent) and then dried in vacuo for 12 hours.

6. General Protocol for Synthesis of 1,4-Benzodiazepine Derivatives on Solid Support A quantity of the dry solid support to which is bound the substituted 2-aminobenzophenone as prepared above, corresponding to structure 2 of Reaction Scheme I above, in which the quantity of substituted 2-aminobenzophenone amounts to 0.5–0.15 mmol, is added to a 50 mL round bottom flask fitted with a stir bar. Approximately 15 mL of DMF is added to the reaction flask and the resulting slurry is stirred for 1 hour at ambient temperature to ensure that the support is solvated. The DMF is then removed by a filtration cannula. To the remaining solvated solid support is added 15 mL of 20% piperidine in DMF, and the resulting yellow slurry is stirred for 20 to 30 minutes at ambient temperature. The solvent is then removed by the filtration cannula and the remaining yellow solid support is rinsed five times in 10 mL DMF and five times in 10 mL CH$_2$Cl$_2$, each washing continuing for approximately thirty seconds with stirring, with cannula filtration between successive washings. This results in the removal of the protecting group from the support-bound 2-aminobenzophenone.

The support with the unprotected 2-aminobenzophenone is now combined with a CH$_2$Cl$_2$ solution containing 0.2M of an FMOC-protected aminoacyl fluoride (with any of various groups for R$^B$) and 0.2M 2,6-di-t-butyl-4-methylpyridine (at least eight-fold excess relative to the molar amount of support-bound 2-aminobenzophenone). After stirring the resulting slurry for 15 hours at ambient temperature, the solution is removed by filtration cannula, and the support-bound intermediate (which corresponds to structure 3 of Reaction Scheme I) is washed three times each with 10 mL CH$_2$Cl$_2$ and 10 mL DMF in the manner described above. A yellow slurry is then formed by adding 15 mL of 20% piperidine in DMF. The slurry is stirred for twenty to thirty minutes at ambient temperature. The solvent is then removed by filtration cannula, and the yellow support is rinsed three times each with 10 mL DMF and 10 mL CH$_2$Cl$_2$ in the manner described above. The resulting intermediate is then diluted with 25 mL of 5% acetic acid in DMF, and the slurry is stirred at 40°–45° C. for 12 hours. The solvent is then removed by filtration cannula, leaving the cyclic product attached to the support, corresponding to structure 4 of Reaction Scheme I. The support is then rinsed three times each with 10 mL DMF and 10 mL freshly dried tetrahydrofuran (THF) in the manner described above. The reaction flask is then sealed with a fresh rubber septum, flushed with nitrogen, and placed under positive nitrogen pressure. Once pressurized, the flask is placed in a −78° C. acetone/dry ice bath.

In a separate flame-dried 25 mL round bottom flask fitted with a stir bar is added 12 mole equivalents of 5-phenylmethyl-2-oxazolidinone relative to the molar amount of the support-bound cyclic product. The flask is then stoppered with a rubber septum and flushed with nitrogen for five minutes, then maintained under positive nitrogen pressure. To the flask is then added freshly distilled THF in a volume appropriate to provide a 0.12M solution of 5-phenylmethyl-2-oxazolidinone in THF. The resulting clear and colorless solution is then cooled to −78° C. and 10 mole equivalents of 2.0M n-butyl lithium in hexanes relative to the molar amount of the support-bound material is then added dropwise with stirring. The solution is then stirred at −78° C. for 15 minutes, and then transferred by cannula to the reaction flask containing the solid support, with stirring at −78° C.

The resulting slurry is stirred at −78° C. for 1.5 hours at which point 15 mole equivalents of the appropriate alkylating agent (the alkyl group corresponding to the substituent R$^C$ in Reaction Scheme I) is added by syringe, followed by approximately 10 mL of anhydrous DMF. The resulting slurry is allowed to warm to ambient temperature with stirring. After 3 hours of stirring at ambient temperature, the solvent is removed by filtration cannula. The support is then washed once with 10 mL THF, twice with 10 mL of 1:1 THF/water, twice with 10 mL THF, and twice with 10 mL CH$_2$Cl$_2$. The product on the solid support at this point is the alkylated benzodiazepine represented by the structure 5 of Reaction Scheme I.

To the solid support is then added 15 mL of 95:5:10 trifluoroacetic acid/water/dimethylsulfide. The resulting slurry is stirred to 3½ hours, then concentrated in vacuo. The yellow solid is then diluted with 5 mL of 1:2 methanol/CH$_2$Cl$_2$ and filtered to remove the solid support. The solid support is then rinsed three times with 5 mL of the same solvent. Concentration of the combined filtrate then provides the unpurified product corresponding to structure 6 of Reaction Scheme I, with a purity of 80–100%. The product is then purified by silica gel chromatography with either methanol (2–10%) in CH$_2$Cl$_2$ or with hexane/ethyl acetate/acetic acid 48–0/50–98/2.

Following this general procedure, the following benzodiazepine derivatives were prepared, the structure of each confirmed as indicated:

7-Chloro-1,3-dihydro-5-(4-hydroxyphenyl)-3-methyl-(2H)1,4-benzodiazepin-2-one (Structure confirmed by proton NMR, carbon-13 NMR, and electron impact mass spectrometry.)

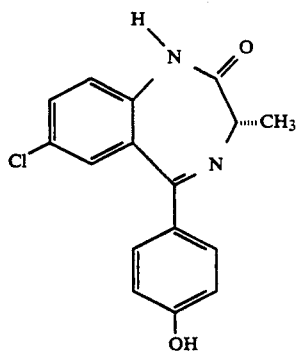

7-Chloro-1,3-dihydro-5-(4-hydroxyphenyl)-1,3-dimethyl-(2H)1,4-benzodiazepin-2-one (Structure confirmed by proton NMR, carbon-13 NMR, and electron impact mass spectrometry.)

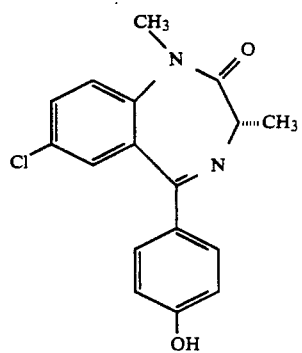

7-Chloro-1,3-dihydro-5-(4-hydroxyphenyl)-1-ethyl-3-methyl-(2H)1,4-benzodiazepin-2-one (Structure confirmed by proton NMR, carbon-13 NMR, and FAB mass spectrometry in m-nitrobenzyl alcohol.)

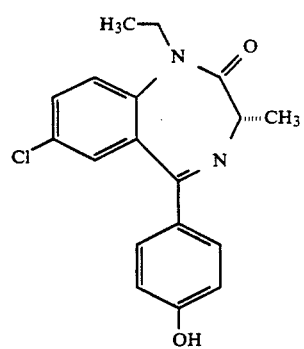

1-Allyl-7-chloro-1,3-dihydro-5-(4-hydroxyphenyl)-3-methyl-(2H)1,4-benzodiazepin-2-one (Structure confirmed by proton NMR, carbon-13 NMR, and FAB mass spectrometry in m-nitrobenzyl alcohol.)

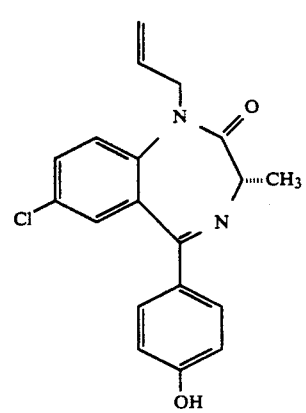

-continued

7-Chloro-1,3-dihydro-5-(4-hydroxyphenyl)-1-ethyl-3-(4-hydroxyphenylmethyl)-(2H)1,4-benzodiazepin-2-one
(Structure confirmed by proton NMR, carbon-13 NMR, and electron impact mass spectrometry.)

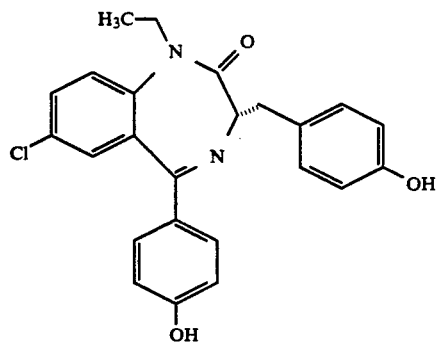

8-Carboxy-7-chloro-1,3-dihydro-1,3-dimethyl-5-phenyl-(2H)1,4-benzodiazepin-2-one
(Structure confirmed by proton NMR and carbon-13 NMR.)

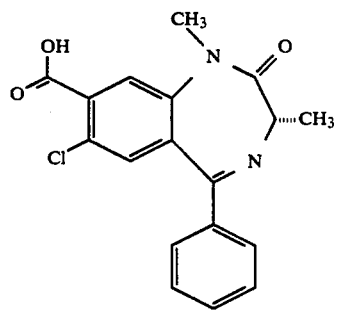

7-Chloro-1,3-dihydro-1-ethyl-5-(4-hydroxyphenyl)-3-isopropyl-(2H)1,4-benzodiazepine-2-one
(Structure confirmed by proton NMR, carbon-13 NMR and FAB mass spectrometry in m-nitrobenzyl alcohol.)

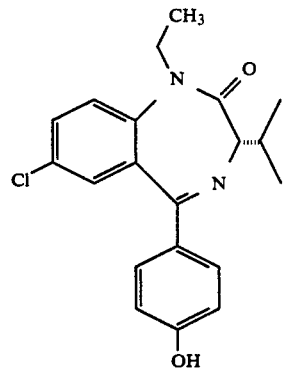

7-Chloro-1,3-dihydro-3-carboxymethyl-1-ethyl-5-(4-hydroxyphenyl)-(2H)1,4-benzodiazepine-2-one
(Structure confirmed by proton NMR, carbon-13 NMR and FAB mass spectrometry in m-nitrobenzyl alcohol.)

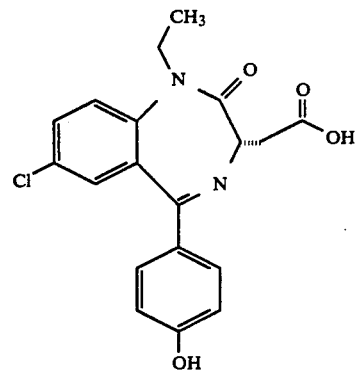

| | |
|---|---|
| 8-Carboxy-7-chloro-1,3-dihydro-1-methyl-5-phenyl-3-phenylmethyl-(2H)1,4-benzodiazepine-2-one (Structure confirmed by proton NMR, carbon-13 NMR and FAB mass spectrometry in m-nitrobenzyl alcohol.) | 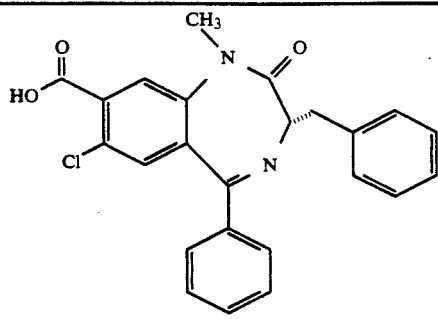 |
| 8-Carboxy-7-chloro-1,3-dihydro-3-methyl-5-phenyl-1-phenylmethyl-(2H)1,4-benzodiazepine-2-one (Structure confirmed by proton NMR, carbon-13 NMR and FAB mass spectrometry in m-nitrobenzyl alcohol.) | 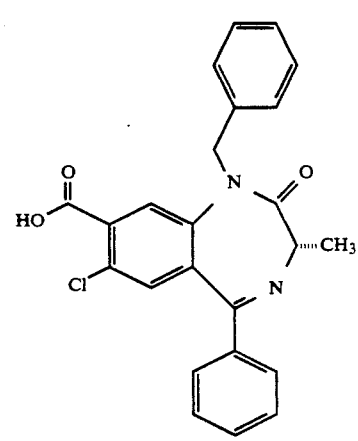 |
| 7-Chloro-1,3-dihydro-1-ethyl-5-(4-hydroxyphenyl)-1-ethyl-3-(4-aminobutyl)-(2H)1,4-benzodiazepine-2-one (Structure confirmed by proton NMR and FAB mass spectrometry in m-nitrobenzyl alcohol.) | 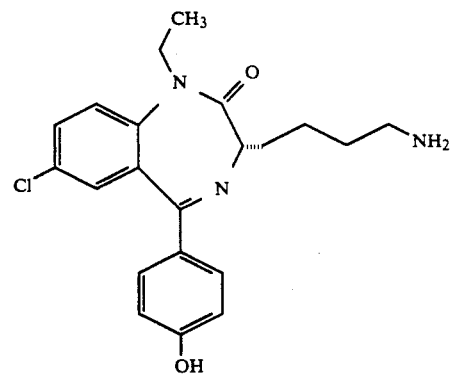 |

7. Racemization Assay

The following assay confirmed that racemization had not occurred during any step of the reaction sequence. The test species were the benzodiazepine derivative (S)- and (R)- iomers of 7-chloro-1,3-dihydro-5-(4-hydroxyphenyl)-1-ethyl-3-methyl-(2H)1,4-benzodiazepin-2-one, the third of the eleven products shown above ($R^A$=Cl at the 7-position on the structure, i.e., para- relative to the amide group, $R^B$=methyl and $R^C$=ethyl).

The (S)-isomer was prepared according to the general protocol described above, using (S)-N-FMOC-alanyl fluoride for amide bond formation and ethyl iodide as the alkylating agent. The benzodiazepine was treated with excess diazomethane in 5:1 THF/methanol for 2 hours to give the methyl ether product. The ether product was evaluated for optical purity by HPLC analysis on a 10 mm×25 cm 3,5-dinitrobenzoylphenylglycine chiral Pirkle column with 2% isopropanol in hexane as the eluent, a flow rate of 6 mL/min and with absorbance monitored at 260 nm. The (S)-benzodiazepine eluted at 22.24 min. None of the (R)-benzodiazepine was observed (i.e., less than 1%), confirming that racemization had not occurred.

The procedure was repeated, except that (R)-N-FMOC-alanyl fluoride was used in place of (S)-N-FMOC-alanyl fluoride. The (R)-benzodiazepine eluted at 21.628 min.

8. Combinatorial Synthesis and Screening

The procedures described in the preceding sections of this example are used in a combinatorial synthesis by using pins in place of the solid phase particles in one embodiment. The removal of reaction solutions and rinses from the support is accomplished by physically lifting the pins out of the reaction solutions which are retained in 96-well Microtiter plates, and dipping them into rinse solutions, rather than employing a filtration cannula. Air- and water-sensitive reactions are conducted in a glove bag or glove box. The benzodiazepine derivatives are cleaved from the pins into the wells of a 96-well Microtiter plate by treatment with the acid cleavage cocktail 95:5:10 trifluoroacetic acid/water/dimethylsulfide. The cleavage cocktail is then removed by employing a Microtiter plate speed vacuum apparatus (such as Savant Speed Vac and Microtiter Rotor, Model #SS). Screening is then performed by any of the standard methods for performing screens on Microtiter plates. These methods represent an adaptation of the methods described by Geysen and coworkers in Geysen et al., *J. of Immunological Methods* (1987) 102:259-274, incorporated herein by reference.

III. Prostaglandins

A. Description

In a similar manner, the invention is applicable to preparing and screening derivatives of prostaglandins, which are local hormones that regulate a wide variety of physiological processes. Naturally occurring prostaglandins and synthetic derivatives have served as important therapeutic agents for treating many physiological disorders. The present invention may be used for the study of prostaglandins with such goals as developing more potent derivatives or developing derivatives specific for disorders for which no known prostaglandins are effective.

Here as well, a solid-phase synthesis method has been developed. An illustration of this method is shown in Reaction Scheme III.

Reaction Scheme) that has been surface-derivatized to include terminal chloromethylphenyl groups 11. A functionalized dihydropyran 12 is coupled to the resin through an alkylative process in accordance with the procedure of Merrifield, as described in Lu et al., *J. Org. Chem.* (1981) 46:3433-3436, to form the further derivatized resin 13. The resin is then reacted with β-hydroxycyclopentenone in the presence of acid to form the coupled product 14. The coupling not only serves to immobilize the β-hydroxycyclopentenone, but also to prevent intermolecular proton transfer between unreacted hydroxycyclopentenone and the enolate which would be formed upon cuprate addition to the hydroxycyclopentenone if the latter were not coupled in this manner.

Alkylation at the 4- and 5-positions on the pentenone ring is then achieved by reaction with $R^E$CuLi (where $R^E$ is alkyl or substituted alkyl) under anhydrous conditions, inert atmosphere and low reaction temperatures, to form the intermediate enolate 15, followed by reaction with an alkyl halide $R^F$X (where $R^F$ is alkyl or substituted alkyl) to form the fully alkylated yet still immobilized prostaglandin derivative 16. Further manipulations can then be performed to extend the range of derivatives. Examples are reduction or addition of alkyl lithiums or grignard reagents, or olefination of the

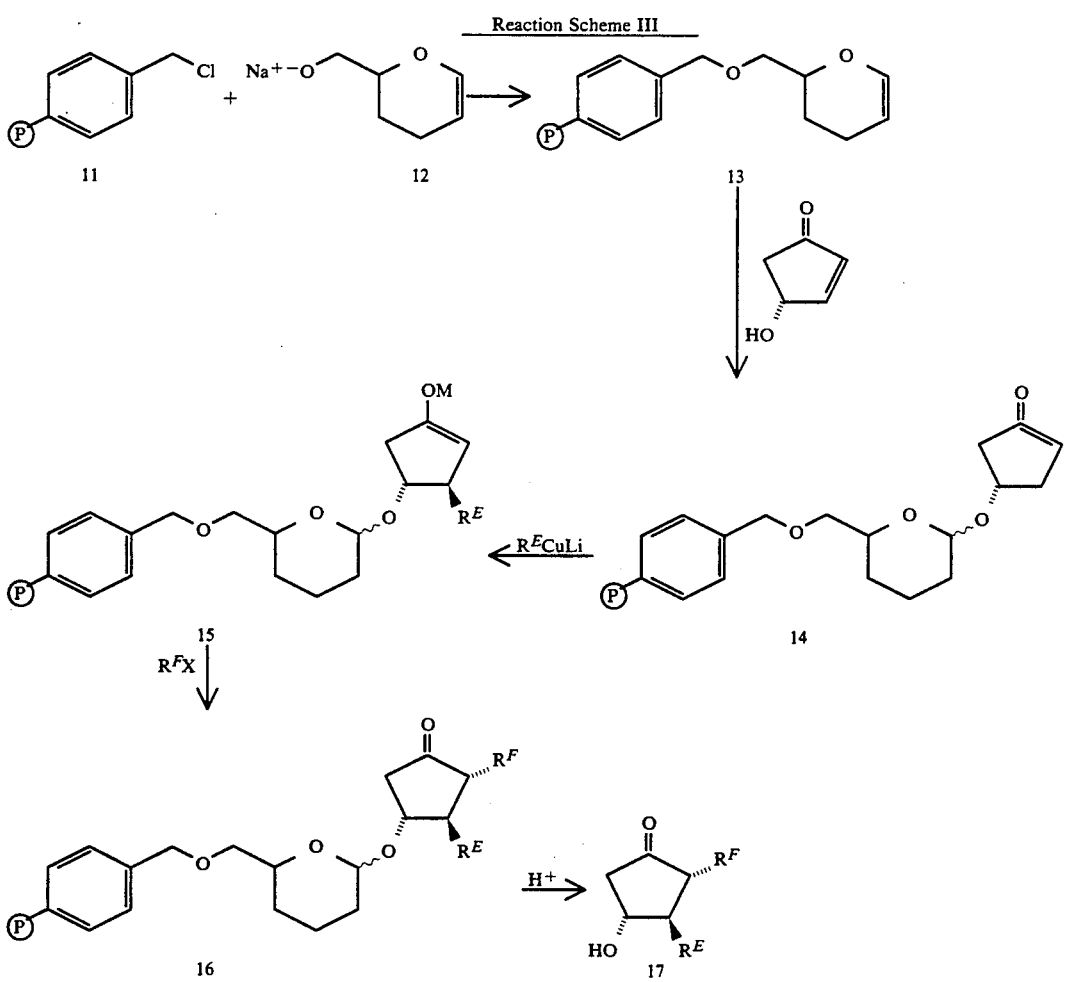

The solid phase in this method is a polystyrene/divinyl benzene resin (represented by the circled P in the ketone functionality, or modification of either or both of the alkyl side chains on the pentanone ring.

Cleavage of the prostaglandin derivative from the resin is readily achieved by treatment with mild acid, to achieve the cleaved product 17.

Screening may then be performed in a manner analogous to that described above for the benzodiazepine derivatives.

B. Examples

The following generalized protocol follows Reaction Scheme III. The protocol describes a solid-phase synthesis using a particulate resin. Translation of the protocol into a combinatorial synthesis and screening is achieved in the same manner described above in the benzodiazepine derivative examples.

1. Preparation of Functionalized Dihydropyran

The compound prepared by this procedure is the sodium salt of 2-hydroxymethyl-3,4-dihydro-2H-pyran, which is compound 12 of Reaction Scheme III.

To a 0.2M solution of (3,4-dihydro-2H-pyran-2-ylmethyl)-3,4-dihydropyran-2H-pyran-2-carboxylate (a commercially available compound) in 2:1 dioxane/water is added 1.5 equivalents of 1N aqueous sodium hydroxide with stirring. The reaction is continued at ambient temperature until complete as confirmed by thin-layer chromatography (TLC). The solvents are then removed in vacuo and the residue is partitioned between 1N aqueous sodium carbonate solution and ethyl acetate. The organic layer is washed twice with sodium carbonate solution and once with aqueous sodium chloride solution, then dried over sodium sulfate and concentrated in vacuo to give the product. If necessary, the product can be purified by silica gel chromatography using ethyl acetate/hexane/triethylamine as eluent.

2. Derivatization of a Solid-Phase Resin with the Functionalized Dihydropyran The derivatized resin of this procedure is shown as structure 13 of Reaction Scheme III.

Chloromethylated polystyrene resin (1% crosslinked divinylbenzene-styrene, 100-200 mesh, substitution levels 0.6-1.0 meq/g) is solvated in three volumes of freshly distilled tetrahydrofuran (from sodium/benzophenone ketyl) with slow stirring under positive nitrogen atmosphere in a flame-dried round bottom flask. In a separate flame-dried flask is added 2-hydroxymethyl-3.4-dihydro-2H-pyran (3.5 mole equivalents relative to meq of chloromethyl groups). The flask is then flushed with nitrogen, then maintained under a positive nitrogen pressure. Freshly distilled THF or dimethylacetamide is then added by syringe until a 0.2M concentration is reached. The solution is then cooled to $-78°$ C. To this solution is added 2.0M n-butyl lithium in hexanes (3.0 mol equivalents relative to meq of chloromethyl groups), dropwise with stirring. The solution is stirred at $-78°$ C. for 0.5 hour, then transferred by cannula with stirring to the solvated support precooled to $-78°$ C. The resulting slurry is then allowed to warm to room temperature with stirring over 1-12 hours. The solution is removed by filtration cannula, and the support is washed once with THF, then three times with $CH_2Cl_2$, then dried in vacuo for 12 hours.

3. Coupling of 4-Hydroxycyclopent-2-en-one to Derivatized Resin

The coupled product of this procedure is shown as structure 14 of Reaction Scheme III.

To a flame-dried round bottom flask fitted with stir bar is added the derivatized support prepared in the preceding section of this example and 5 mole equivalents of 4-hydroxycyclopent-2-en-one. After flushing with nitrogen, freshly distilled $CH_2Cl_2$ is added until the solution is 0.2-0.5M in hydroxycyclopentenone. Toluenesulfonic acid (0.05-0.5 mole equivalents) is added with stirring for 1-24 hours. The solution is then removed by filtration cannula, and the support is washed five times with $CH_2Cl_2$, then dried in vacuo.

4. Cuprate Addition and Alkylation

This procedure continues Reaction Scheme III through intermediates 15 and 16 to product 17.

The support-bound hydroxycyclopentenone prepared in the last section of this example is placed in a flame-dried round bottom flask fitted with stir bar. The flask is stoppered, then flushed with argon. Three volumes of freshly distilled THF are added by syringe, and the resulting slurry is stirred for 0.5 hour to solvate the resin. The reaction flask is then cooled to $-78°$ C.

In a separate flask, the alkyl cuprate (5 mole equivalents relative to the support-bound hydroxycyclopentenone) is prepared according to the procedure of Noyori (Suzuki et al., *J. Am. Chem. Soc.* (1988) 110:4722). The cuprate solution is transferred by Teflon cannula to the reaction flask with stirring at $-78°$ C., to which some HMPA linker may also be added if desired. The solution is stirred at $-78°$ C. for 1 hour, then gradually allowed to warm to $-30°$ C., and stirred at this temperature for 0.5-5 hours. The solvent is then removed by filtration cannula, and freshly distilled dimethoxyethane is added to the reaction flask by syringe, followed by 10 mole equivalents of the alkylating agent. The reaction mixture is stirred at $-30°$ C. for 1-24 hours, then allowed to warm to $0°$ C. and stirred at this temperature for 0-12 hours. The solution is removed by filtration cannula, and the support is then washed twice with THF, twice with 1:1 THF/water, twice with THF, and finally twice with $CH_2Cl_2$. The desired product is then cleaved from the support by dilution with a THF/dilute aqueous acetic acid solution, with stirring, for 0.5-5 hours. The product may be isolated by extraction with ethyl acetate, and purified by silica gel chromatography.

IV. β-Turn Mimetics

A. Description

A third example of a class of compounds to which the present invention may be applied are β-turn mimetics. These are compounds having molecular structures similar to β-turns which are one of three major motifs in a protein's molecular architecture. As one of the structural motifs, β-turns play a critical role in protein-ligand and protein-protein interactions. This role often takes the form of recognition between peptide hormones and their respective receptors. The development of a combinatorial library of β-turn mimetics will provide potential therapeutic agents whose activity is a result of the enhanced affinity between the β-turn structure and its receptor.

β-turns are loosely defined as a reverse in the direction of a peptide chain which takes place over four amino acid residues. A number of β-turns have been classified based on the geometries observed along the peptide backbone. Examples of a generic β-turn 21 and a generic β-turn mimetic 22 are shown below.

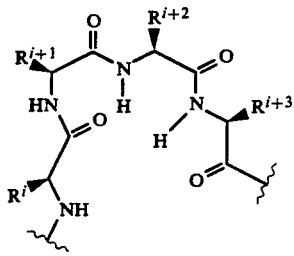

21

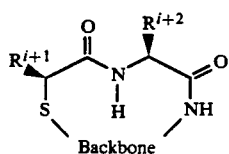

22

While orientation of side chains i+1 and i+2 is critical for receptor recognition, significant structural variations exist along the β-turn backbone which affect the relative orientations of these side chains. The vast number of spatial combinations possible for these side chains has resulted in tremendous difficulty in identifying the optimal structure of a β-turn mimetic for high affinity binding to a specific receptor. This problem can now be addressed by the synthesis and screening of a combinatorial library of β-turn mimetics which encompasses virtually all possible side-chain combinations and multiple orientations for each combination.

To apply the methods of this invention to β-turn mimetics 22, a solid-phase synthesis strategy has been developed, as outlined in Reaction Scheme IV.

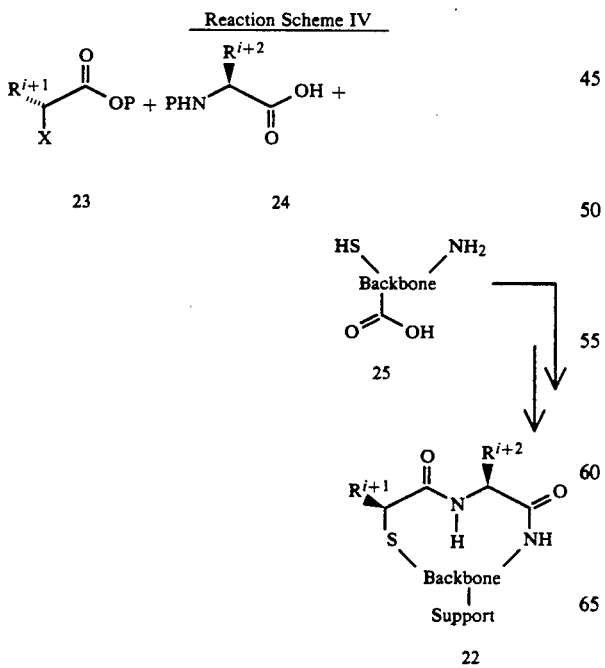

The components required to introduce the amino acid side-chains of the mimetic include the protected amino acids themselves 24 and α-halo acids or esters 23 which are available in one step from the corresponding amino acids or esters. See, Evans et al., *J. Am. Chem. Soc.* (1989) 111:1063–1072, and Koppenhoefer et al., *Organic Synthesis* (1987) 66:151–159, incorporated herein by reference. Utilizing both (R) and (S) enantiomers of components 23 and 24 increases the diversity in side-chain orientations which are synthesized. A third component 25 serves to define the geometry of the two side-chains and further provides a site for attachment to a solid support. Examples of readily available derivatives of component 25 are shown below.

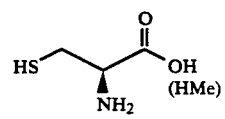

25a

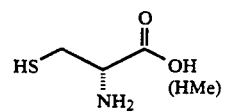

25b

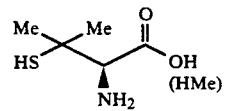

25c

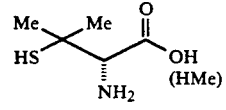

25d

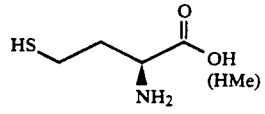

25e

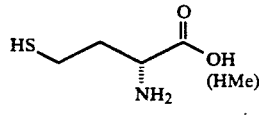

25f

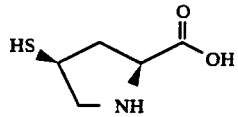

25g

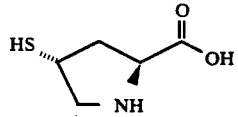

25h

Because many derivatives of each of the components 23–25 are available or can be synthesized in very few steps, a large combinatorial library based upon β-turn mimetics can be constructed rapidly and efficiently.

A more complete synthesis route to 22 is shown in Reaction Scheme V.

Reaction Scheme V

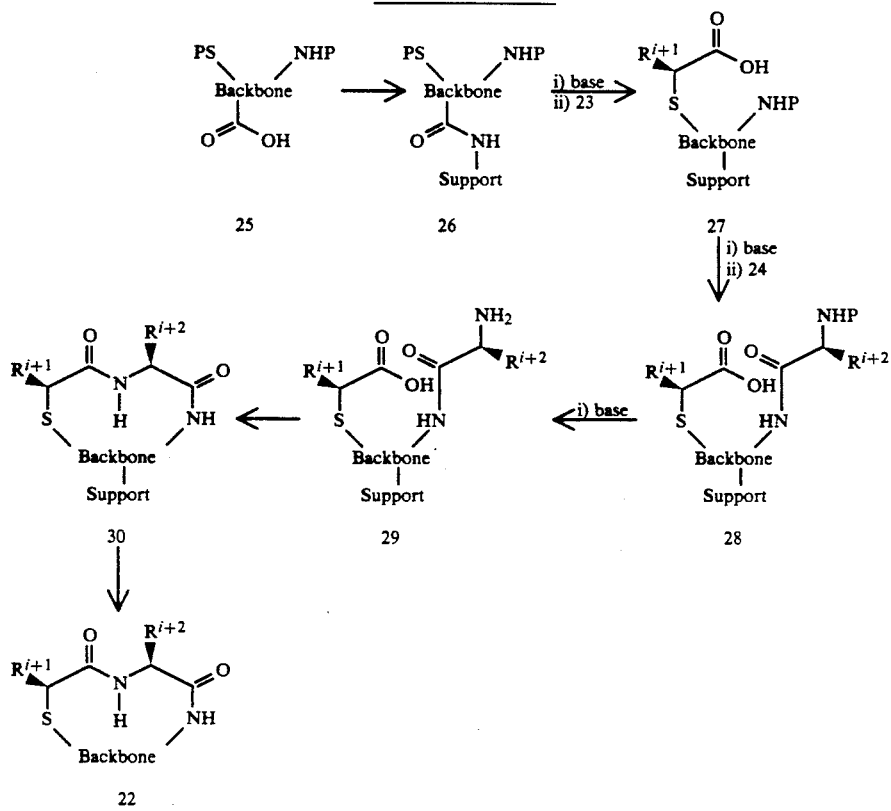

The particular couplings en route to 22 are all well precedented. Initial coupling of the backbone component 25 (having both amine and thiol functionalities in their protected form) with a solid support to yield 26 can be achieved using amide forming reactions which are well known in the art. Subsequent alkylations between α-halo acids or esters and the thiolate anion of deprotected 26 (formed by treatment with base) can be carried out without racemization of the chiral centers using the methods employed by several groups for similar alkylations. See, Benovitz et al., *Peptides* (1985) 6:648; Nicolaides et al., *J. Med. Chem.* (1986) 29:959–971 (1986); and Spatola et al., *J. Org. Chem.* (1981) 46:2393– 2394 (1981). Further coupling of 24 and deprotected 27 to form 28 is accomplished by again employing standard methods for amide bond formation in solid phase synthesis. Removal of the amine protecting group provides 29. Macrocyclization involving the amine and carboxylic acid functionalities of 29 produces the solid supported β-turn mimetic 30 and can be carried out using the method of Felix et al., *Int. J. Pept. Protein Res.* (1988) 31:231–238 and 32:441–454. Finally, removal of the solid support furnishes the β-turn mimetic 22. Each of the reference publications cited above is incorporated herein by reference.

A combinatorial library of different combinations of the substituent groups $R^{i+1}$ and $R^{i+2}$ is developed in a manner analogous to that described above for the benzodiazepines and prostaglandins. Screening and cleavage are then likewise conducted in an analogous manner.

B. EXAMPLES

The following generalized protocol follows Reaction Scheme V. The protocol describes a solid-phase synthesis using a particulate resin. Translation of the protocol into a combinatorial synthesis and screening is achieved in the same manner described above in the benzodiazepine derivative examples.

1. Coupling the Backbone to the Support

The structure prepared in this procedure is structure 26 of Reaction Scheme V.

A peptide reaction flask is charged with aminomethyl resin (1.91 g, 1.51 mmol of crosslinked divinylbenzene-styrene, 200–400 mesh size, substitution level 0.79 milliequivalents/g), two equivalents of an S-fluorenylmethyl protected, N-fluorenylmethoxycarbonyl protected cysteine analog (having the structure of the desired backbone), and hydroxybenzotriazole (2.2 equivalents). Anhydrous DMF is then added to provide a solution 0.2–0.4M in the protected cysteine derivative. The resulting mixture is vortexed for 0.5 hour to fully solvate the resin. Either diisopropylcarbodiimide or benzotriazol-1-yl-oxy-tris(dimethylamino)-phosphonium hexafluorophosphate (2.2 equivalents) is then added by syringe. The reaction flask is stoppered and then vortexed until the Kaiser ninhydrin test on approximately 10 mg of the solid support demonstrates that coupling is complete (approximately 24 hours). The solvent and agents are then filtered away from the solid support and the support is rinsed five times with 20 mL dimethylformamide and five times with 20 mL $CH_2Cl_2$, then dried in vacuo for 12 hours.

2. Removal of the Protecting Groups From the Support-Bound Backbone (26) and Coupling to the α-Halo Acid (23) and the α-Amino Acid (24)

This procedure results in structure 28.

The product of the Section 1 of this example is added to a round bottom flask fitted with stir bar and filtration cannula. The flask is flushed with nitrogen, and then degassed 50% piperidine in DMF is added by the cannula. The resulting slurry is stirred for 2-24 hours at ambient temperature, and the solution is then removed by the cannula. The support is then washed five times with DMF, following which a degassed 0.2-0.5M solution of 10 equivalents of sodium phenoxide or ethoxide in 2:1 ethanol/DMF is added. The appropriate protected α-halo acid (structure 23, 5 mole equivalents) is then added, with stirring. The resulting slurry is stirred under a nitrogen atmosphere for 1-24 hours. The solution is then removed by the cannula, and the support is washed with 5% acetic acid in DMF, followed by three times with DMF and twice with $CH_2Cl_2$. The support-bound intermediate (structure 27) is then diluted with a solution 0.2M in the pentafluorophenyl ester of the appropriate FMOC-protected α-amino acid (structure 24) and 0.2M in diisopropylethylamine in DMF. The resulting mixture is stirred until the Kaiser ninhydrin test shows that a free amine is no longer present (2-24 hours). The solution is then removed by the cannula and the support is washed three times each with DMF and $CH_2Cl_2$.

3. Cyclization to the β-Turn Mimetic

The support-bound intermediate (structure 28) prepared above is treated with 20% piperidine in DMF for twenty minutes. This results in support-bound intermediate 29. The solution is then removed by the cannula, and the remaining support is washed five times each with DMF and $CH_2Cl_2$. Cyclization is then performed by adding a 0.025-0.2M solution of benzotriazol-1-yl-oxytris(dimethylamino)-phosphonium hexafluorophosphate (BOPCl) in DMF and stirring for 4-12 hours, followed by removal of the solution by the cannula. The BOPCl solution is then added again, stirring is continued for another 4 hours and the solution removed. This process is repeated until no free amines are observed as indicated by a Kaiser test. The result is the support-bound product 30.

V. Pin Based Synthesis

Preferably, the techniques described above are used to synthesize more than 3, preferably more than 5, preferably more than 10, more preferably more than 50, more preferably more than 100, and more preferably more than 1,000 different molecules simultaneously. FIG. 1 illustrates apparatus for preparation of the various compositions described herein. Such apparatus is described in greater detail in association with the synthesis of peptides in Geysen et al., *J. Immun. Methods* (1987) 102:259-274, incorporated herein by reference for all purposes. The method utilizes a substrate 102 having a plurality of pins or other extensions 104. The pins are each inserted simultaneously into individual reagent containers 106 in tray 108. It will be recognized that only a few pins/trays are shown in FIG. 1, but in most embodiments a large array of such pins/containers will be provided. In a common embodiment, an array of 96 pins/containers is utilized.

Each tray is filled with a particular reagent for coupling in a particular chemical reaction on an individual pin. Accordingly, the trays will often contain different reagents. Since the chemistry disclosed herein has been established such that a relatively similar set of reaction conditions may be utilized to perform each of the reactions, it becomes possible to conduct multiple chemical coupling steps simultaneously.

Figure 2:
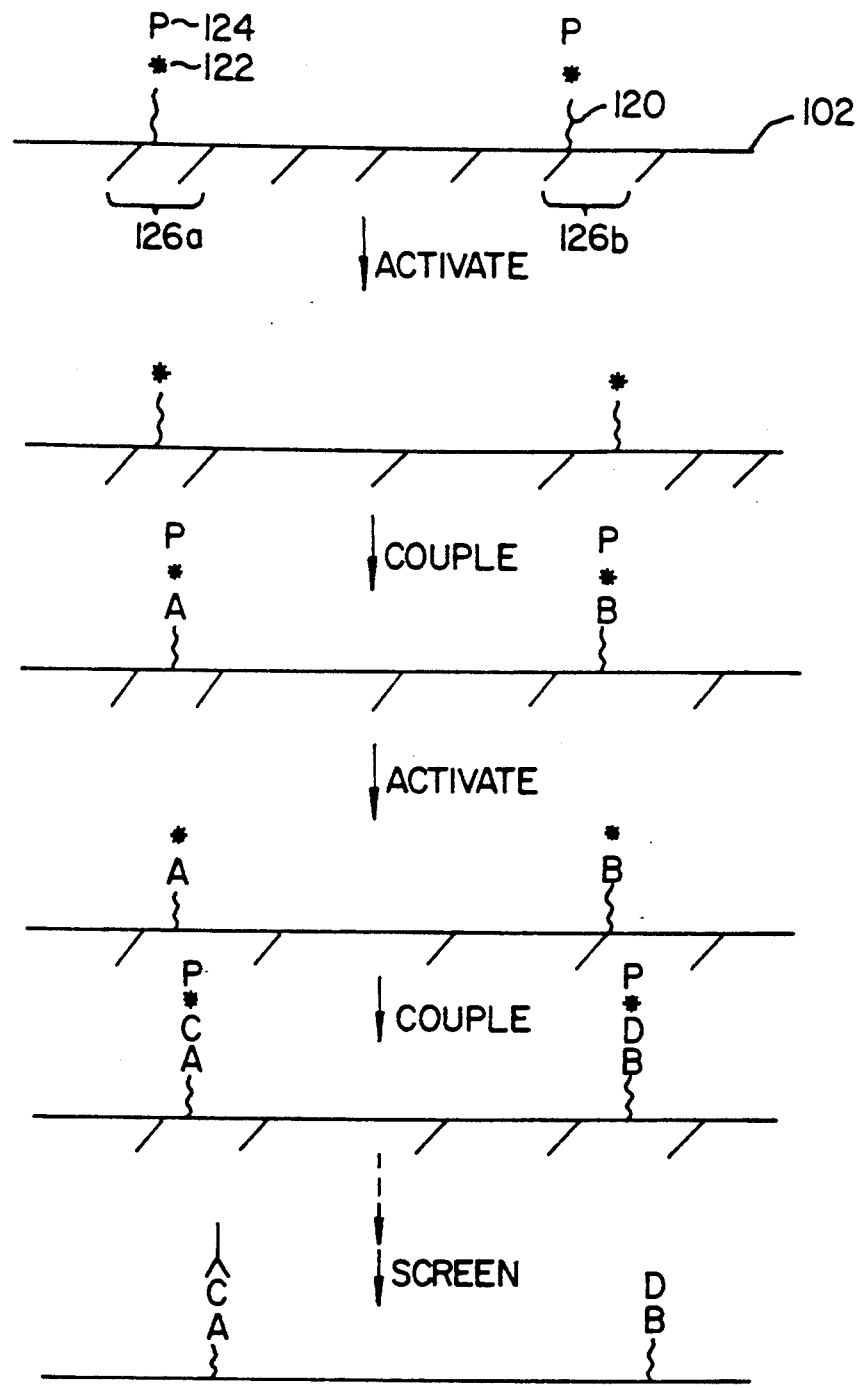
FIG. 2 illustrates the method of forming diverse molecules according to the methods herein.

FIG. 2 illustrates the method utilized to form the various molecules discussed herein. As shown, in the first step of the process the invention provides for the use of substrate(s) on which the chemical coupling steps are conducted. As shown therein, the substrate is optionally provided with linker molecules 120 having active sites 122. In the particular case of benzodiazepines, for example, the linker molecules may be selected from a wide variety of molecules such as HMPA. The active sites are optionally protected initially by protecting groups 124. Among a wide variety of protecting groups are materials such as FMOC, BOC, t-butyl esters, t-butyl ethers, and the like. Various exemplary protecting groups are described in, for example, Atherton et al., *Solid Phase Peptide Synthesis*, IRL Press (1989), incorporated herein by reference. In some embodiments, the linker molecule may provide for a cleavable function by way of, for example, exposure to acid or base.

The substrate includes a plurality of spatially addressable regions such as 126a and 126b. In the particular embodiment described herein, the regions 126a and 126b are pins extending from a common substrate.

In an initial step, one or more of the regions of the substrate are activated by removal of the protecting groups. It will be recognized that both regions may be activated in some embodiments simultaneously, or the regions may be individually activated. In the case of pin-based techniques, the regions may be activated by, for example, dipping selected pins in trays having an appropriate activating agent. In the particular case of acid labile protecting groups, such activating agents may include acid, while in the case of base labile groups, such agents may include base.

Thereafter, a first portion of a molecule to be synthesized is added to the support. In the particular case of benzodiazepine synthesis, for example, the first portion will be a substituted amino benzophenone in many cases. The first portion of the molecule to be synthesized is provided with an active site, such as an amino site in the case of amino benzophenones, which is preferably protected by an appropriate protecting group. The protecting group on the first portion of the molecule to be synthesized will in some cases be the same as the protecting group on the substrate, although in many cases a different protecting group will be utilized. Appropriate protecting groups for an amino group on an amino benzophenone are described in Atherton et al., previously incorporated herein by reference. In the case of pin-based synthesis the first portion of the molecule to be added is coupled by way of dipping the appropriate pins in an a tray having containers with the appropriate material to be added. In most cases, the various regions will be coupled to different molecules, represented by A and B in FIG. 2. For example, in the case of benzodiazepine synthesis, A and B will be represented by different amino benzophenones.

A and B will be coupled at the same time in many embodiments, although the regions 126a and 126b may, alternatively, be activated at different times, in which case the entire surface may be washed with, for example, A after region 126a is activated followed by activation of region 126b and washing of both regions with B. Since A and B are also protected, undesirable coupling will not take place in the regions where it is not desirable. It will be recognized by those of skill in the art that additional steps of washing and the like will be desirable in some embodiments, but are not illustrated in FIG. 1 for the sake of simplicity.

Thereafter, an additional activation step is conducted by removal of the protecting groups from the molecule portions A and B either at the same or different times. In the case of FMOC protecting groups, for example, such activation will be conducted by exposure to, for example, a basic solution. Thereafter, an additional coupling step is performed in which molecule portions C and D are added to the molecule portions A and B respectively. In the particular case of benzodiazepine synthesis, for example, the molecule portions C and D will be represented by activated acyl fluoride derivatives of FMOC-protected natural or unnatural amino acids.

Thereafter, optional additional coupling steps, cyclization steps, or the like are performed on the growing molecules. For example, in the case of benzodiazepines, the additional steps will normally include removal of the FMOC protecting group using base followed by exposure to 5% acetic acid in DMF for cyclization, followed by alkyation of the amide nitrogen.

Since a wide array of substituted amino benzophenone groups, and a wide array of acyl fluoride amino acid derivatives are readily available, the synthesis technique herein results in an array of materials on the substrate that are at known locations on the substrate and which may be effectively used in screening studies to determine which of the synthesized materials show significant affinity for a receptor or receptors of interest. As shown in FIG. 2, receptor affinity is studied by exposing the substrate to the receptor or receptors of interest, and determining where the receptor has bound to the substrate. In some embodiments, the location of the receptor on the substrate may be conveniently located by labelling the receptor with an radioactive or fluorescent label, and scanning the surface of the substrate for the presence of the receptor. In some embodiments, the receptor of interest may be unlabelled, but later exposed to a second receptor that is labelled and known to be complementary to the receptor of interest. As indicated in FIG. 2, the receptor will bind to the molecules that are complementary to the receptor (such as AB in FIG. 1) while it will not bind to other molecules on the substrate (such as BD in FIG. 1). Accordingly, the present method provides an effective way to identify ligands that are complementary to a receptor.

In alternative embodiments, the synthesized benzodiazepine is cleaved and screened in solution, using the methods described in detail above.

VI. Bead Based Synthesis

In an alternative embodiment of the invention a similar series of chemical coupling/cyclization steps are conducted, except that the synthesis steps are conducted on discrete solid substrates such as beads. A general approach for bead based synthesis in conjunction with peptides is described in Lam et al., "A new type of synthetic peptide library for identifying ligand-binding activity," *Nature* (1991) 354:82-84, incorporated herein by reference for all purposes, and further described in PCT application no. 92/00091 and Houghten et al., "Generation and use of Synthetic Peptide Combinatorial Libraries for Basic Research and Drug Discovery," *Nature* (1991) 354:84-86, and also incorporated herein by reference for all purposes.

Figure 3:
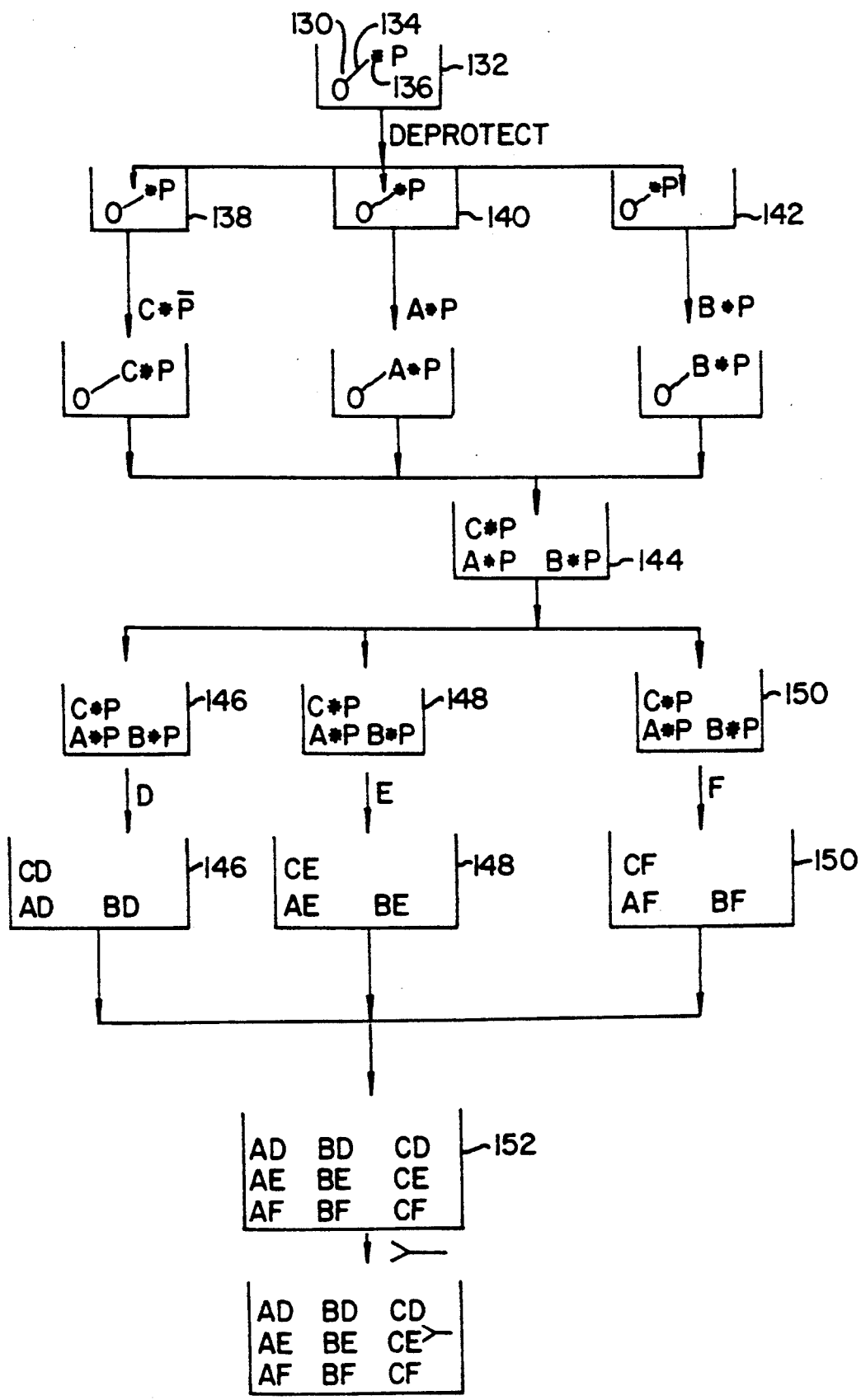
FIG. 3 illustrates bead based synthesis.

FIG. 3 illustrates the synthesis of molecules such as benzodiazepines on such beads. A large plurality of beads 130 are suspended in a suitable carrier (such as water) in a container 132. Although only a single bead is illustrated in FIG. 3 for the purposes of simplifying the illustration, it will be recognized that a large number of beads are utilized. The beads are provided with optional linker molecules 134 having an active site 136. The active site is protected by an optional protecting group P.

In a first step of the synthesis, the beads are divided for coupling into containers 138, 140, and 142. The protecting groups are then removed and a first portion of the molecule to be synthesized is added to the various containers. For example, in the case of benzodiazepines, the first portion of the molecule to be synthesized may be various FMOC protected substituted amino benzophenones, represented herein by A, B, and C. The first portion of the molecules to be synthesized comprise active sites protected by a protecting group P.

Thereafter, the various beads are appropriately washed of excess reagents, and remixed in container 144. Again, it will be recognized that by virtue of the large number of beads utilized at the outset, there will similarly be a large number of beads randomly dispersed in the container 144, each having a particular first portion of the monomer to be synthesized on a surface thereof. For the purpose of simplifying the illustration, the beads and linker molecules are not shown in the bottom portion of FIG. 3.

Thereafter, the various beads are again divided for coupling in containers 146, 148, and 150. The beads in container 146 are deprotected and exposed to a second portion of the molecule to be synthesized, represented by D, while the beads in the containers 148 and 150 are coupled to molecule portions E and F respectively. In the particular case of benzodiazepine synthesis, molecule portions D, E, and F would be, for example, acyl fluoride derivatives of natural or natural amino acids. Accordingly, molecules AD, BD, and CD will be present in container 146, while AE, BE, and CE will be present in container 148, and molecules AF, BF, and CF will be present in container 150. Each bead, however, will have only a single type of molecule on its surface. In the particular embodiment shown in FIG. 3, all of the possible molecules formed from the first portions A, B, C, and the second portions D, E, and F have been formed.

Optionally, the beads are then recombined into container 52. Additional steps such as cyclization, and the like are conducted on the completed polymer molecules.

Thereafter, the beads are exposed to a receptor of interest. In a preferred embodiment the receptor is fluorescently or radioactively labelled. Thereafter, one or more beads are identified that exhibit significant levels of, for example, fluorescence using one of a variety of techniques. For example, in one embodiment, mechanical separation under a microscope is utilized. The identity of the molecule on the surface of such separated beads is then identified using, for example, NMR, electron impact mass spectrometry, or the like.

In alternative embodiments the identity of the molecule that is complementary to the receptor is determined with respect to the "bin" or container in which the labelled receptor is located. For example, by exposing the molecules in containers 146, 148, and 150 to the labelled receptor, the identity of one terminal portion of the molecule may be identified. For example, if fluorescence is noted after exposure to the molecules in container 146, but not 148 or 150, it is readily determined that the terminal molecule that produces a complementary receptor is "D." Thereafter, one will synthesize all of the molecules AD, BD, and CD in separate containers. The identity of the other terminal portion of the molecule can then be determined by identifying where receptor binding is located among these molecules.

VII. Light Directed Synthesis

Figure 4:
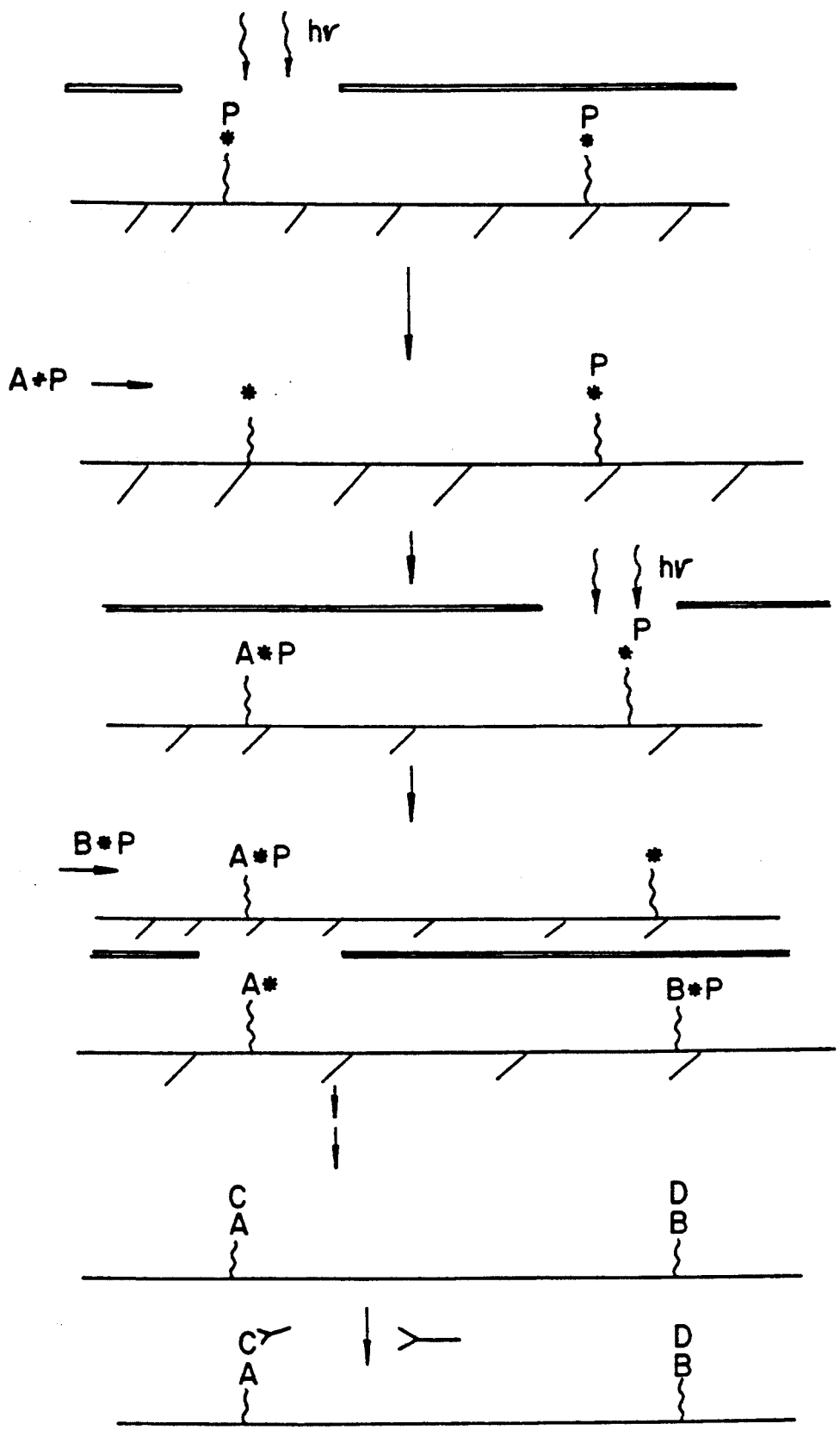
FIG. 4 illustrates light based synthesis.

In an alternative embodiment, different $\beta$-turn mimetics or other materials are synthesized on a substrate using light directed techniques as shown in FIG. 4, preferably using wavelengths of light greater than 400 nm and more preferably more than 500 nm. As shown therein, the substrate is similarly provided with protecting groups, optionally coupled to the substrate via linker molecules. In this case, the protecting groups are removable upon exposure to light. Accordingly, the protecting groups in a first selected region are removed by exposing the first selected region to light, but not exposing the second selected region to light. As illustrated in FIG. 4, this selective irradiation step may be accomplished through the use of a mask such as the masks commonly used in the semiconductor industry. Such techniques are described in greater detail in U.S. Pat. No. 5,143,854 (Pirrung et al.), incorporated herein by reference for all purposes.

Thereafter, the entire substrate or a part thereof is exposed to a first portion of the molecule to be synthesized (indicated by A in FIG. 4). In the case of benzodiazepines, the first portion of the molecule will, for example, be substituted amino benzophenones with appropriate light, base, or acid labile protecting groups. Thereafter, second regions of the substrate are exposed to light using the same or a different mask, and B is coupled to these regions. Coupling of the portions C and D follows in a similar manner, wherein C and D are representative of, for example, activated acyl fluoride derivatives of FMOC protected amino acids.

In a similar manner to that shown in FIG. 1, the substrate is then exposed to a receptor of interest that is appropriately labelled with, or coupled to another receptor with a label, such as a fluorescent or radioactive label. The substrate is then scanned to determine the location of the label. From knowledge of the composition of the molecule synthesized at each site, it becomes possible to identify the molecule(s) that are complementary to the receptor.

VIII. Conclusion

The above description is illustrative and not restrictive. Many variations of the invention will become apparent to those of skill in the art upon review of this disclosure. Merely by way of example a wide variety of process times, reaction temperatures, and other reaction conditions may be utilized, as well as a different ordering of certain processing steps. The scope of the invention should, therefore, be determined not with reference to the above description, but instead should be determined with reference to the appended claims along with their full scope of equivalents.

What is claimed is:

1. A method of making a plurality of benzodiazepines on a substrate comprising the steps of:
    coupling substituted amino benzophenones to a substrate, said substituted amino benzophenones comprising protecting groups;
    removing said protecting groups from said amino benzophenones to form amino benzophenones having amino active sites;
    coupling a plurality of amino acid derivatives to said amino active sites; and
    cyclizing molecules resulting from the step of coupling said plurality of amino acid derivatives, whereby a plurality of benzodiazepines are formed on said substrate.

2. The method as recited in claim 1 further comprising the step of alkylating the benzodiazepines.

3. The method as recited in claim 1 wherein the step of coupling substituted amino benzophenones to a substrate further comprises the steps of:
    coupling the substituted amino benzophenones to acid-cleavable linkers;
    and coupling the acid-cleavable linkers to the substrate.

4. The method as recited in claim 3 wherein the linkers are coupled to the substituted amino benzophenone before the linkers are coupled to the substrate.

5. The method as recited in claim 3 wherein the linkers are coupled to the substrate before the linkers are coupled to the substituted amino benzophenone.

6. The method as recited in claim 1 wherein the step of coupling substituted amino benzophenones to a substrate further comprises the steps of:
    activating a first region of the substrate;
    coupling a first substituted amino benzophenone to said first region;
    activating a second region of the substrate; and
    coupling a second substituted amino benzophenone to said second region.

7. The method as recited in claim 2 wherein the step of coupling substituted amino benzophenones to a substrate further comprises the steps of:
    activating a first region of the substrate;
    coupling a first substituted amino benzophenone to said first region;
    activating a second region of the substrate; and
    coupling a second substituted amino benzophenone to said second region.

8. The method as recited in claim 1 wherein the step of coupling a plurality of amino acid derivatives further comprises the steps of:
    treating one portion of the amino benzophenones having amino active sites with a first amino acid;
    and treating a second portion of the amino benzophenones having amino active sites with a second amino acid, whereby a mixture of coupled benzophenone derivatives is formed on said substrate.

9. The method as recited in claim 2 wherein the step of coupling a plurality of amino acid derivatives further comprises the steps of:
    treating one portion of the amino benzophenones having amino active sites with a first amino acid;
    and treating a second portion of the amino benzophenones having amino active sites with a second amino acid, whereby a mixture of coupled benzophenone derivatives is formed on said substrate.

10. The method as recited in claim 1 wherein the step of removing said protecting groups from said amino benzophenones further comprises the steps of:

removing one portion of said protecting groups from said amino benzophenones, whereby a mixture of protected and deprotected amino benzophenones is produced;

coupling an amino acid derivative to where said protecting group has been removed; and removing a second portion of said protecting groups from said amino benzophenones.

11. The method as recited in claim 2 wherein the step of removing said protecting groups from said amino benzophenones further comprises the steps of:

removing one portion of said protecting groups from said amino benzophenones, whereby a mixture of protected and deprotected amino benzophenones is produced;

coupling an amino acid derivative to where said protecting group has been removed; and removing a second portion of said protecting groups from said amino benzophenones.

12. The method as recited in claim 2 wherein the step of alkylating the cyclized molecules further comprises the steps of:

treating one portion of the cyclized molecules with a first alkylating agent;

and treating a second portion of the cyclized molecules with a second alkylating agent, whereby a mixture of alkylated molecules is formed on said substrate.

13. The method as recited in claim 7 wherein the step of alkylating the cyclized molecules further comprises the steps of:

treating one portion of the cyclized molecules with a first alkylating agent;

and treating a second portion of the cyclized molecules with a second alkylating agent, whereby a mixture of alkylated molecules is formed on said substrate.

14. The method as recited in claim 11 wherein the step of alkylating the cyclized molecules further comprises the steps of:

treating one portion of the cyclized molecules with a first alkylating agent;

and treating a second portion of the cyclized molecules with a second alkylating agent, whereby a mixture of alkylated molecules is formed on said substrate.

15. The method as recited in claim 3 wherein linkers are selected from the group consisting of: 4-(4-(5-chloro-2-fluorenylmethoxycarbonylamino-benzoyl)-phenoxymethyl)phenoxyacetic acid and 4-benzoyl-6-chloro-3-fluorenylmethoxycarbonylaminobenzoyloxymethyl-phenoxyacetic acid.

16. The method as recited in claim 2 wherein the alkylated benzodiazepines are selected from the group consisting of:

7-chloro-1,3-dihydro-5-(4-hydroxyphenyl)-1,3-dimethyl-(2H)1,4-benzodiazepin-2-one; 7-chloro-1,3-dihydro-5-(4-hydroxyphenyl)-1-ethyl-3-methyl-(2H)1,4-benzodiazepin-2-one; 1-allyl-7-chloro-1,3-dihydro-5-(4-hydroxyphenyl)-3-methyl-(2H)1,4-benzodiazepin-2-one; 7-chloro-1,3-dihydro-5-(4-hydroxyphenyl)-1-ethyl-3-(4-hydroxyphenylmethyl)-(2H)1,4-benzodiazepin-2-one; 8-carboxy-7-chloro-1,3-dihydro-1,3-dimethyl-5-phenyl-(2H)1,4-benzodiazepin-2-one; 7-chloro-1,3-dihydro-1-ethyl-5-(4-hydroxyphenyl)-3-isopropyl-(2H)1,4-benzodiazepine-2-one; 7-chloro-1,3-dihydro-3-carboxymethyl-1-ethyl-5-(4-hydroxyphenyl)-(2H)1,4-benzodiazepine-2-one; 8-carboxy-7-chloro-1,3-dihydro-1-methyl-5-phenyl-3-phenylmethyl-(2H)1,4-benzodiazepine-2-one; 8-carboxy-7-chloro-1,3-dihydro-3-methyl-5-phenyl-1-phenylmethyl-(2H)1,4-benzodiazepine-2-one; and 7-chloro-1,3-dihydro-1-ethyl-5-(4-hydroxyphenyl)-1-ethyl-3-(4-aminobutyl)-(2H)1,4-benzodiazepine-2-one.

17. The method as recited in claim 3 wherein said acid-cleavable linkers are selected from the group consisting of allyl 2-(4-hydroxymethylphenoxy) acetate and allyl 2-(4-bromomethylphenoxy) acetate.

18. The method of claims 1 or 3, wherein said coupling of substituted benzophenones to a substrate comprises coupling the phenyl rings of said benzophenones to said substrate.

* * * * *